(12) United States Patent
Sookraj

(10) Patent No.: US 12,152,004 B2
(45) Date of Patent: Nov. 26, 2024

(54) SYSTEMS AND PROCESSES FOR PRODUCING ORGANIC ACIDS DIRECTLY FROM BETA-LACTONES

(71) Applicant: Novomer, Inc., Rochester, NY (US)

(72) Inventor: Sadesh H. Sookraj, Rochester, NY (US)

(73) Assignee: Novomer, Inc., Rochester, NY (US)

( * ) Notice: Subject to any disclaimer, the term of this patent is extended or adjusted under 35 U.S.C. 154(b) by 980 days.

(21) Appl. No.: 17/054,811

(22) PCT Filed: Jun. 25, 2019

(86) PCT No.: PCT/US2019/039001
§ 371 (c)(1),
(2) Date: Nov. 12, 2020

(87) PCT Pub. No.: WO2020/005951
PCT Pub. Date: Jan. 2, 2020

(65) Prior Publication Data
US 2021/0221762 A1 Jul. 22, 2021

Related U.S. Application Data

(63) Continuation of application No. 16/023,410, filed on Jun. 29, 2018, now abandoned, which is a continuation-in-part of application No. 15/640,197, filed on Jun. 30, 2017, now abandoned, which is a continuation-in-part of application No. 15/464,346, filed on Mar. 21, 2017, now Pat. No. 10,662,139.

(60) Provisional application No. 62/311,262, filed on Mar. 21, 2016.

(51) Int. Cl.
| | | |
|---|---|---|
| C07C 51/09 | (2006.01) | |
| B01J 3/00 | (2006.01) | |
| B01J 8/06 | (2006.01) | |
| C07C 67/28 | (2006.01) | |
| C07C 231/12 | (2006.01) | |
| C07C 309/22 | (2006.01) | |
| C07D 307/54 | (2006.01) | |
| C07D 317/30 | (2006.01) | |
| C07F 7/18 | (2006.01) | |

(52) U.S. Cl.
CPC .............. *C07C 51/09* (2013.01); *B01J 3/006* (2013.01); *B01J 8/067* (2013.01); *C07C 67/28* (2013.01); *C07C 231/12* (2013.01); *C07C 309/22* (2013.01); *C07D 307/54* (2013.01); *C07D 317/30* (2013.01); *C07F 7/1804* (2013.01); *C07F 7/1892* (2013.01); *B01J 2219/0004* (2013.01)

(58) Field of Classification Search
CPC ....... C07C 51/09; C07C 67/28; C07C 231/12; C07C 309/22; C07C 57/04; B01J 3/006; B01J 8/067; B01J 2219/0004; C07D 307/54; C07D 317/30; C07F 7/1804; C07F 7/1892; Y02P 20/58; Y02P 20/582
See application file for complete search history.

(56) References Cited

U.S. PATENT DOCUMENTS

| | | | |
|---|---|---|---|
| 3,176,042 A | 3/1965 | Schnizer | |
| 3,462,484 A | 8/1969 | Schnizer et al. | |
| 3,689,533 A | 9/1972 | Schultz et al. | |
| 3,849,457 A | 11/1974 | Haag | |
| 3,932,500 A | 1/1976 | Duembgen et al. | |
| 4,929,798 A * | 5/1990 | de Lasa ................ | C10G 3/49 585/920 |
| 5,198,578 A | 3/1993 | Etzkorn et al. | |
| 5,412,112 A | 5/1995 | Wang et al. | |
| 8,445,703 B2 | 5/2013 | Allen et al. | |
| 8,796,475 B2 | 8/2014 | Allen et al. | |
| 8,961,909 B2 | 2/2015 | Lehr et al. | |
| 9,096,510 B2 | 8/2015 | Porcelli et al. | |
| 9,156,803 B2 | 10/2015 | Allen et al. | |
| 9,206,144 B2 | 12/2015 | Allen et al. | |
| 9,327,280 B2 | 5/2016 | Lee et al. | |
| 9,403,788 B2 | 8/2016 | Lee et al. | |
| 9,493,391 B2 | 11/2016 | Allen et al. | |
| 9,914,689 B2 | 3/2018 | Porcelli et al. | |
| 10,662,139 B2 | 5/2020 | Sookraj et al. | |
| 2008/0143957 A1* | 6/2008 | Linhardt ................ | C08J 7/056 351/159.05 |
| 2008/0161624 A1 | 7/2008 | Glover et al. | |
| 2010/0113822 A1 | 5/2010 | Craciun et al. | |
| 2011/0319849 A1 | 12/2011 | Collias et al. | |

(Continued)

FOREIGN PATENT DOCUMENTS

| | | |
|---|---|---|
| CN | 1915957 A | 2/2007 |
| CN | 103987682 A | 8/2014 |

(Continued)

OTHER PUBLICATIONS

Werther, J., "Fluidized Bed Reactors." Ullmann's Encyclopedia of Industrial Chemistry 2007 p. 319-366.*
Henkel, K., "Reactor Types and Their Industrial Applications." Ullmann's Encyclopedia of Industrial Chemistry, 2012; p. 1-36.*
Faujasite Subgroup_ Mineral information, data and localities 2023 (http://www.mindat.org/min-35126.html) p. 1-9.*
Machine-generated English-language translation of JP2003173088A.
Levy, Leon B., Journal of Polymer Science: Part A: Polymer Chemistry, vol. 30, 1992, pp. 569-576.
Search Report for co-pending Taiwanese Application TW106109417; date of completion: Jul. 24, 2020; 7 pages.

(Continued)

*Primary Examiner* — John M Mauro
(74) *Attorney, Agent, or Firm* — Young Basile Hanlon & MacFarlane, P.C.

(57) ABSTRACT

Provided herein are reactor systems and processes for producing organic acids directly from beta-lactones. Such reactor systems and processes involve the use of a heterogeneous catalyst, such as a zeolite at vapor phase conditions. The reactor systems and processes may use a fixed bed, moving bed or fluidized contacting zone as reactor configurations.

20 Claims, 4 Drawing Sheets

(56) References Cited

U.S. PATENT DOCUMENTS

| | | |
|---|---|---|
| 2012/0123137 A1 | 5/2012 | Allen et al. |
| 2012/0315681 A1 | 12/2012 | van Walsem et al. |
| 2013/0165670 A1 | 6/2013 | Allen et al. |
| 2013/0281715 A1 | 10/2013 | Allen et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0183708 A1 | 7/2015 | Harris et al. |
| 2015/0299083 A1 | 10/2015 | Porcelli et al. |
| 2015/0307437 A1 | 10/2015 | Ziemian et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0282251 A1 | 10/2018 | Sookraj |

FOREIGN PATENT DOCUMENTS

| | | |
|---|---|---|
| CN | 104350034 A | 2/2015 |
| CN | 106831389 A | 6/2017 |
| GB | 922177 A | 3/1963 |
| JP | S601205 A | 1/1985 |
| JP | S61213206 A | 9/1986 |
| JP | 2009035508 A | 2/2009 |
| JP | 2013173088 A | 9/2013 |
| WO | 199407835 A1 | 4/1994 |
| WO | 2010/118128 A1 | 10/2010 |
| WO | 2012/030619 A1 | 3/2012 |
| WO | 2012134397 A1 | 10/2012 |
| WO | 2012/158573 A1 | 11/2012 |
| WO | 2013/063191 A1 | 5/2013 |
| WO | 2013/122905 A1 | 8/2013 |
| WO | 2013/126375 A1 | 8/2013 |
| WO | 2013185009 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165344 A1 | 9/2017 |
| WO | 2017/165345 A1 | 9/2017 |
| WO | 2017165323 A1 | 9/2017 |
| WO | 2018/085251 A1 | 5/2018 |
| WO | 2018/085254 A1 | 5/2018 |
| WO | 2018/136638 A1 | 7/2018 |
| WO | 2018/170006 A1 | 9/2018 |

OTHER PUBLICATIONS

Beta Analytic Testing Laboratory, Understanding Carbon-14 Analysis, Biobased Analysis—Radiocarbon Dating or carbon 14, dated Sep. 20, 2018 https://www.betalabservices.com/biobased/barconl4-dating.html <http://www.betalabservices.com/biobased/barconl4-dating.html> (2 pages).

Fan et al., Ethylene Formation by Catalytic Dehydration of Ethanol with Industrial Considerations, Materials, Dec. 28, 2012, pp. 101-115, vol. 6, Issue 1 (15 pages).

Deactivation behavior, Nafe, Journal of Catalysis 329 (2015) 413-424.

Potassium-Ion-Exchanged, Yan et al., ACS Catalysis (2017) 538-550.

Beta Analytic, published 2009 (Year: 2009).

International Search Report from co-pending PCT application PCT/US2019/039001. Date of mailing: Nov. 7, 2019. Four pages.

Written Opinion of the ISA for co-pending PCT Application PCT/US2019/039001. Date of mailing: Nov. 7, 2019. Nine pages.

Fujisawa et al., "One-Step Synthesis of w-Hydroxycarboxylic Acids By the Reaction Of w-Metaloxylated Grignard Reagents With B-Propiolactones." Chemistry Letters, vol. 11, No. 4, 1982 (2 pages).

Kawashima et al., "A facile method for synthesis of three carbon-homologated carboxylic acid by regioselective ring-opening of ß-propiolactones with organocopper reagents, tetrahedron." vol. 45, Issue 2, 1989.

Office Action issued in co-pending Application No. SA520420910 dated May 14, 2023 with English translation (15 pages).

International Preliminary Report on Patentability for co-pending application PCT/US2019/039001. Date of issuance of report: Dec. 29, 2020.

Japanese Office Action for Application No. 2018-549537, dated Mar. 9, 2021.

Office Action issued in co-pending Application No. JP2020-573354 mailed May 30, 2023 (33 pages).

Zhu, Rui et al., "A Comprehensive Study on Metal Triflates Promoted Hydrogenolysis of Lactones to Carboxylic Acids: From Both Synthetic and Mechanistic Perspectives", ACS Catalysis, 2017, 7(11), 7520-7528, DOI: 10.1021/acscatal.7b01569.

Chinese Office Action and Search Report for Application No. 201780018126, dated Apr. 16, 2021.

Office Action issued in co-pending Japanese Application 2020-573354 dated Oct. 24, 2023 (with English translation). 18 pages.

Notice of Reasons For Rejection (Office Action) dispatched Jun. 4, 2024 in co-pending Application JP2020-573354 (English Translation).

\* cited by examiner

SYSTEMS AND PROCESSES FOR PRODUCING ORGANIC ACIDS DIRECTLY FROM BETA-LACTONES

CROSS-REFERENCE TO RELATED APPLICATIONS

This application is a National Stage Filing under 35 USC 371 of the PCT Application No. PCT/US2019/039001 filed 29 Jun. 2019, published as WO2020/005951, which claims priority to U.S. patent application Ser. No. 16/023,410, filed Jun. 29, 2018, which is a continuation-in-part of U.S. patent application Ser. No. 15/640,197, filed Jun. 30, 2017, which is a continuation-in-part of U.S. patent application Ser. No. 15/464,346, filed Mar. 21, 2017, which claims benefit of U.S. Provisional Application No. 62/311,262, filed Mar. 21, 2016, all of which are incorporated herein by reference in their entirety for all purposes.

FIELD

This invention generally relates to reactor systems and processes for producing organic acids directly form beta-lactones.

BACKGROUND

The production and use of organic acids such as acrylic acid (AA) has grown significantly in recent decades as the demand for polyorganic acids such as polyacrylic acid-based superabsorbent polymers (SAPs) has grown. SAPs are used extensively for the manufacture of diapers, adult incontinence products, and feminine hygiene products, as well as in agricultural applications.

Currently, commercial acrylic acid is typically derived from propylene oxidation. Propylene is primarily a product of oil refining and its price and availability are closely tied to crude oil prices. Because of this, acrylic acid prices remain tied closely to the price of oil and its fluctuations.

Thus, there exists a need in the art for alternative methods to synthesize certain organic acids. At the same time, it would be preferred to produce organic acids from renewable resources. U.S. patent application publications 2015/0183708 published Jul. 2, 2015 and 2014/0018574 filed Jan. 15, 2014 disclose the production of bio-based acrylic acid from poly-3-hydroxypropionate using a wide variety of biologically active materials.

Other references disclose producing acrylic acid from beta-propiolactone with inorganic catalysts. U.S. Pat. No. 3,176,042 disclosed a phosphoric acid catalyzed process to produce acrylic acid from beta-propiolactone. Due to corrosiveness of phosphoric acid and slow reaction rate this process is capital intensive. Additionally, water must be fed to the reactor continuously to maintain the composition of phosphoric acid inside the reactor at the desired levels. This leads to the need to separate water from the produced acrylic acid resulting in additional equipment and operating costs.

U.S. Pat. No. 9,096,510 B2 teaches production of acrylic acid from beta-propiolactone using a solid catalyst in at least partial gas phase conditions.

WO20133191 teaches production of acrylic acid from beta-propiolactone in a two-step process: at first beta-propiolactone is polymerized to produce poly-propiolactone and then acrylic acid is produced via thermolysis of poly-propiolactone. This process capital intensive and has high operating costs as highly exothermic polymerization reaction is followed by highly endothermic thermolysis reaction.

Thus, improved methods are sought to produce certain organic acid products, especially high purity organic acid products from non-hydrocarbon and preferably renewable sources.

BRIEF SUMMARY

The reactor systems and processes described herein solve an existing need in the art for producing higher purity organic acid products from beta-lactone reagents. Advantageously, the reactor systems and processes of the present invention provide higher purity organic acid products from beta-lactone reagents and are economically favorable compared to processes of the prior art.

One object of the present invention is to provide processes that produce at least one organic acid product from at least one beta-lactone reagent.

Another object of the present invention is to provide reactor systems that are configured to produce at least one highly pure organic acid product from at least one beta-lactone reagent through the processes of the present invention.

Provided herein are systems and processes for producing organic acid products from beta-lactone reagents via an improved one-step process that is economically favorable compared to the processes known in the art. The reactor systems and processes of the present invention include combining a beta-lactone reagent, a heterogenous catalyst, and optionally a solvent or diluent for reaction in a vessel. The reactor systems and processes include maintaining the beta-lactone reagent and any solvent or diluent in a vapor phase while contacting the heterogenous catalyst to produce an organic acid product.

In preferred embodiments, the heterogeneous catalyst comprises a crystalline microporous solid. Catalysts of the type that are specifically suited for this invention include alkaline-earth phosphates, supported phosphate salts, calcium hydroxyapatites, inorganic salts, metal oxides, and zeolites. In preferred embodiments, the heterogeneous catalyst is an alumina-silicate molecular sieve and more preferably a zeolite having Lewis or Brönsted acidity. The zeolites can be in hydrogen form or in cation exchanged form with suitable cations, for example, alkali metals such as Na+ or K+ and alkali-earth cations such as $Ca^{2+}$, $Mg^{2+}$, $Sr^{2+}$, or $Ba^{2+}$; $Zn^{2+}$, Cu+, and $Cu^{2+}$.

In certain preferred embodiments, the processes for producing organic acids from beta-lactones may be performed using reactor systems configured to include fixed bed continuous reactor and regeneration. In certain preferred embodiments, the processes for producing organic acids from beta-lactones may be performed using reactor systems configured for passing vapor phase feed streams to a fixed bed of zeolite catalyst. In certain preferred embodiments, beta-lactones may be diluted with inert solvents and/or inert gases prior to reaction.

DESCRIPTION OF THE FIGURES

The present application can be best understood by reference to the following description taken in conjunction with the accompanying figures included in the specification.

DETAILED DESCRIPTION

Figure 1:
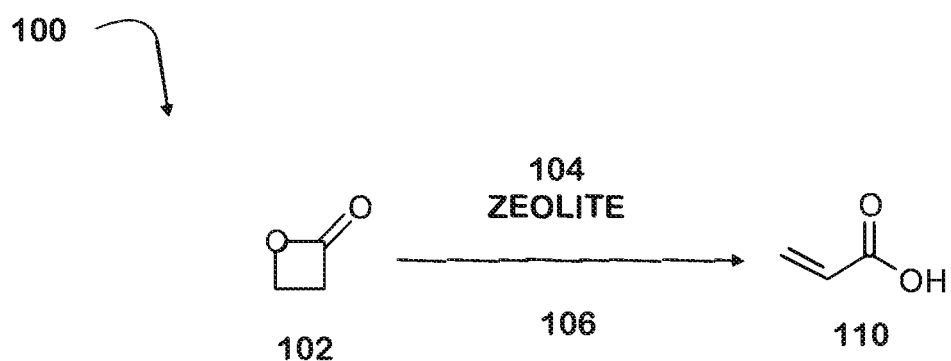
FIG. 1 depicts an exemplary process to produce an organic acid product from a beta-lactone reagent.

The following description sets forth exemplary systems, processes, parameters and the like. It should be recognized, however, that such description is not intended as a limitation on the scope of the present disclosure but is instead provided as a description of exemplary aspects.

Definitions

The term "polymer", as used herein, refers to a molecule of high relative molecular mass, the structure of which comprises the multiple repetition of units derived, actually or conceptually, from molecules of low relative molecular mass. In some aspects, a polymer is comprised of only one monomer species. In some aspects, a polymer is a copolymer, terpolymer, heteropolymer, block copolymer, or tapered heteropolymer of one or more epoxides.

The terms bio-content and bio-based content mean biogenic carbon also known as bio-mass derived carbon, carbon waste streams, and carbon from municipal solid waste. In some variations, bio-content (also referred to as "bio-based content") can be determined based on the following:

Bio-content or Bio-based content=[Bio (Organic) Carbon]/[Total (Organic) Carbon] 100%, as determined by ASTM D6866 (Standard Test Methods for Determining the Bio-based (biogenic) Content of Solid, Liquid, and Gaseous Samples Using Radiocarbon Analysis).

As disclosed in US 20170002136, the ASTM D6866 method allows the determination of the bio-based content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This 14 C is immediately oxidized into carbon dioxide, and represents a small, but measurable fraction of atmospheric carbon. Atmospheric carbon dioxide is cycled by green plants to make organic molecules during photosynthesis. The cycle is completed when the green plants or other forms of life metabolize the organic molecules producing carbon dioxide which is then able to return back to the atmosphere. Virtually all forms of life on Earth depend on this green plant production of organic molecules to produce the chemical energy that facilitates growth and reproduction. Therefore, the 14C that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See also WO 2009/155086.

The application of ASTM D6866 to derive a "bio-based content" is built on the same concepts as radiocarbon dating, but without use of the age equations. The analysis is performed by deriving a ratio of the amount of radiocarbon (14C) in an unknown sample to that of a modern reference standard. The ratio is reported as a percentage, with the units "pMC" (percent modern carbon). If the material being analyzed is a mixture of present day radiocarbon and fossil carbon (containing no radiocarbon), then the pMC value obtained correlates directly to the amount of bio-based material present in the sample. The modern reference standard used in radiocarbon dating is a NIST (National Institute of Standards and Technology) standard with a known radiocarbon content equivalent approximately to the year AD 1950. The year AD 1950 was chosen because it represented a time prior to thermonuclear weapons testing which introduced large amounts of excess radiocarbon into the atmosphere with each explosion (termed "bomb carbon"). The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Petroleum-based carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), they may have at least about 99 pMC, including about 100 pMC.

Combining fossil carbon with present day carbon into a material will result in a dilution of the present day pMC content. By presuming that 107.5 pMC represents present day bio-based materials and 0 pMC represents petroleum derivatives, the measured pMC value for that material will reflect the proportions of the two component types. A material derived 100% from present day biomass would give a radiocarbon signature near 107.5 pMC. If that material were diluted with 50% petroleum derivatives, it would give a radiocarbon signature near 54 pMC.

A bio-based content result is derived by assigning 100% equal to 107.5 pMC and 0% equal to 0 pMC. In this regard, a sample measuring 99 pMC will give an equivalent bio-based content result of 93%.

Assessment of the materials described herein according to the present embodiments is performed in accordance with ASTM D6866 revision 12 (i.e. ASTM D6866-12), the entirety of which is herein incorporated by reference. In some embodiments, the assessments are performed according to the procedures of Method B of ASTM-D6866-12. The mean values encompass an absolute range of 6% (plus and minus 3% on either side of the bio-based content value) to account for variations in end-component radiocarbon signatures. It is presumed that all materials are present day or fossil in origin and that the desired result is the amount of bio-based carbon "present" in the material, not the amount of bio-material "used" in the manufacturing process.

Other techniques for assessing the bio-based content of materials are described in, for example, U.S. Pat. Nos. 3,885,155, 4,427,884, 4,973,841, 5,438,194, and 5,661,299, and WO 2009/155086.

The bio-content of the organic acids produced by thermolysis of the one or more polylactone products may be based on the bio-content of the one or more epoxide reagents and carbon monoxide reagents. For example, in some variations of the processes described herein, the one or more epoxide reagents and carbon monoxide reagents described herein may have a bio-content of greater than 0%, and less than 100%. In certain variations of the processes described herein, the one or more epoxide reagents and carbon monoxide reagents described herein may have a bio-content of at least 10%, at least 20%, at least 30%, at least 40%, at least 50%, at least 60%, at least 70%, at least 80%, at least 90%, at least 95%, at least 96%, at least 97%, at least 98%, at least 99%, at least 99.5%, at least 99.9%, at least 99.99%, or 100%. In certain variations, one or more epoxide reagents and carbon monoxide reagents derived from renewable sources may be used. In other variations, at least a portion of the one or more epoxide reagents and carbon monoxide reagents used is derived from renewable sources, and at least a portion of the one or more epoxide reagents and carbon monoxide reagents is derived from non-renewable sources.

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987; the entire contents of each of which are incorporated herein by reference.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-30 carbon atoms. In some aspects, aliphatic groups contain 1-12 carbon atoms. In some aspects, aliphatic groups contain 1-8 carbon atoms. In some aspects, aliphatic groups contain 1-6 carbon atoms. In some aspects, aliphatic groups contain 1-5 carbon atoms, in some aspects, aliphatic groups contain 1-4 carbon atoms, in yet other aspects aliphatic groups contain 1-3 carbon atoms, and in yet other aspects, aliphatic groups contain 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "acrylate" or "acrylates" as used herein refer to any acyl group having a vinyl group adjacent to the acyl carbonyl. The terms encompass mono-, di- and tri-substituted vinyl groups. Examples of acrylates include, but are not limited to: acrylate, methacrylate, ethacrylate, cinnamate (3-phenylacrylate), crotonate, tiglate, and senecioate.

The term "unsaturated", as used herein, means that a moiety has one or more double or triple bonds.

The term "alkyl," as used herein, refers to saturated, straight- or branched-chain hydrocarbon radicals derived from an aliphatic moiety containing between one and six carbon atoms by removal of a single hydrogen atom. Unless otherwise specified, alkyl groups contain 1-12 carbon atoms. In some aspects, alkyl groups contain 1-8 carbon atoms. In some aspects, alkyl groups contain 1-6 carbon atoms. In some aspects, alkyl groups contain 1-5 carbon atoms, in some aspects, alkyl groups contain 1-4 carbon atoms, in yet other aspects, alkyl groups contain 1-3 carbon atoms, and in yet other aspects alkyl groups contain 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned may include those that result in the formation of stable or chemically feasible compounds. The term "stable", as used herein, refers to compounds that are not substantially altered when subjected to conditions to allow for their production, detection, and, in some aspects, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

As used herein, the term "catalyst" refers to a substance the presence of which increases the rate of a chemical reaction, while not being consumed or undergoing a permanent chemical change itself.

Renewable sources means a source of carbon and/or hydrogen obtained from biological life forms that can replenish itself in less than one hundred years.

Renewable carbon means carbon obtained from biological life forms that can replenish itself in less than one hundred years.

Recycled sources mean carbon and/or hydrogen recovered from a previous use in a manufactured article.

Recycled carbon means carbon recovered from a previous use in a manufactured article.

As used herein, the term "about" preceding one or more numerical values means the numerical value ±5%. It should be understood that reference to "about" a value or parameter herein includes (and describes) aspects that are directed to that value or parameter per se. For example, description referring to "about x" includes description of "x" per se.

Further, it should be understood that reference to "between" two values or parameters herein includes (and describes) aspects that include those two values or parameters per se. For example, description referring to "between x and y" includes description of "x" and "y" per se.

The mass fractions disclosed herein can be converted to wt % by multiplying by 100.

Processes for Producing Organic Acids

In some aspects, provided are processes for producing at least one organic acid product from at least one beta-lactone reagent. In some embodiments, the beta-lactone reagents are represented by the following formula:

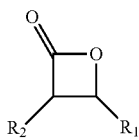

wherein $R_1$ and $R_2$ are independently selected from the group consisting of H, alkyl, alkenyl, alkoxy, alkynyl, cycloalkyl, cycloalkenyl and cycloalkynyl, and wherein both of $R_1$ and $R_2$ are not H at the same time.

In some variations of the beta-lactone reagents used in the processes described herein, one of $R_1$ and $R_2$ is H, and the other of $R_1$ and $R_2$ is alkyl. In one variation, $R_1$ is alkyl, and $R_2$ is H.

In some embodiments, the processes include introducing at least one beta-lactone reagent to at least one reaction vessel; contacting the at least one beta-lactone reagent with at least one heterogenous catalyst in the at least one reaction vessel to produce at least one organic acid; and removing the at least one organic acid from the at least one reaction vessel to provide at least one organic acid product. Such processes may produce organic acid products in high yields, by minimizing other by-products that may form, such as polylactones and polyorganic acids. Such methods produce at least one organic acid product from at least one beta-lactone reagent in a single step reaction.

FIG. 1 illustrates a process of producing at least one organic acid product from at least one beta-lactone reagent, by combining a beta-lactone reagent, a zeolite heterogenous catalyst, and optionally a polymerization inhibitor; and producing acrylic acid. In FIG. 1, beta-propiolactone 102 is introduced to a reaction vessel and contacted with zeolite heterogenous reagent 104 and polymerization inhibitor 106 to produce acrylic acid 110, which is removed from the reaction vessel. In some embodiments, process 100 is performed neat. In other variations, process 100 is performed in the presence of a solvent.

In certain embodiments, a different beta-lactone reagent may be used in the process exemplified in FIG. 1, in place of beta-propiolactone 102. For example, any of the substituted beta-propiolactone compounds described herein may be used. In some variations of the processes and systems described herein, the beta-lactone reagent used is a beta-propiolactone reagent. In certain variations, the beta-propiolactone reagent is a substituted beta-propiolactone compound. In certain variations, the beta-propiolactone reagent is beta-propiolactone compound substituted with at least one alkyl. In one variation, the beta-propiolactone reagent is beta-propiolactone compound substituted with at least one C1-10 alkyl. In one variation, the beta-propiolactone reagent is beta-propiolactone compound substituted with at least one methyl, ethyl or propyl. In certain variations of the foregoing, the beta-propiolactone compound is substituted with one or more substituents, to the extent chemically feasible. In one variation, the beta-propiolactone compound is substituted with one substituent. For example, in one variation, the beta-propiolactone compound is substituted with one methyl group.

In certain preferred embodiments, the processes include: adjusting the operating pressure to reaction conditions for at least one reaction vessel to provide at least one pressure controlled reaction vessel; heating to reaction conditions at least one reaction vessel to provide a temperature controlled reaction vessel; introducing at least one heterogenous catalyst to at least one reaction vessel to provide at least one catalyst charged reaction vessel; and/or dissolving at least one beta-lactone reagent in a solvent to provide at least one diluted beta-lactone reagent.

In preferred embodiments of the present invention, the processes include controlling the rate of the at least one beta-lactone reagent introduced to the at least one reaction vessel. In certain preferred embodiments, the processes include controlling the rate of addition of the at least one beta-lactone reagent to decrease the production of undesirable products. In certain embodiments, the processes include controlling the rate of addition of the at least one beta-lactone reagent to minimize or suppress production of polyorganic acids.

The amount of the at least one beta-lactone reagent introduced to the at least one reaction vessel may be metered by any suitable methods or techniques in the art. The suitable methods or techniques may vary with the scale of production. For example, the suitable methods or techniques may range from adding the at least one beta-lactone reagent in lab scale quantities by metering into the at least one reaction vessel via a needle valve to large scale addition through one or more valve and manifold arrangements. In certain embodiments, fixed-bed reactors and moving-bed reactors may have a throughput in a range of relative weight hourly space velocity (WHSV) of the at least one beta-lactone reagent between 0.4 to 2.1 $h^{-1}$ or between 0.9 to 1.6 $h^{-1}$.

In preferred embodiments, the processes of the present invention may include metering the at least one organic acid removed to produce the at least one organic acid product. In certain preferred embodiments, metering the removal of the at least one organic acid produced may affect the yield of the at least one organic acid product. In certain embodiments, metering the removal of the at least one organic acid produced may increase yield of the at least one acid product. In some embodiments, the metering the removal of the at least one organic acid minimizes polymerization of the at least one organic acid, and thus, formation of polyorganic acid.

In certain preferred embodiments, the at least one organic acid may be removed at elevated temperatures, for example, the temperature is at least 100° C., at least 150° C., at least 200° C., at least 250° C. or at least 300° C. and may be in a range of between 100° C. to 300° C., between 200° C. and 250° C., and or between 250° C. and 300° C.

In certain preferred embodiments, the processes for producing the at least one organic acid product have a yield of at least 50%, at least 55%, at least 60%, at least 65%, at least 70%, at least 75%, at least 80%, at least 85%, at least 90%, or at least 95%.

In preferred embodiments, the processes produce at least one organic acid product that is an unsaturated aliphatic carboxylic acid having purity of at least 95%, at least 96%, at least 97%, or at least 98%. In some variations where the organic acid product produced is isolated, e.g., by distillation, the organic acid product has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%. In certain preferred embodiments, the at least one organic acid product includes at least one vinyl group and at least one carboxylic acid group.

Reactor Systems for Producing Organic Acids

In other aspects, provided are reactor systems used for producing at least one organic acid product from at least one beta-lactone reagent, wherein the at least one beta-lactone reagent is represented by the following formula:

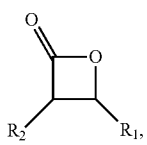

wherein $R_1$ and $R_2$ are independently selected from the group consisting of H, alkyl, alkenyl, alkoxy, alkynyl, cycloalkyl, cycloalkenyl and cycloalkynyl, and wherein both of $R_1$ and $R_2$ are not H at the same time.

In some variations of the beta-lactone reagents used in the reactor systems described herein, one of $R_1$ and $R_2$ is H, and the other of $R_1$ and $R_2$ is alkyl. In one variation, $R_1$ is alkyl, and $R_2$ is H.

In some embodiments, the systems include at least one reaction vessel. In preferred embodiments, the at least one reaction vessel comprises a continuous fixed-bed reactor or a fluidized bed reactor. The at least one reaction vessel may define an interior volume for receiving material from at least one feed stream and a retaining volume adapted for retaining matter in solid, liquid, and gaseous phases. In some embodiments, the at least one reaction vessel may be connected to at least one heater for providing heat to the matter in the retaining volume. In some embodiments, the at least one reaction vessel may be connected to at least one heater.

In some variations, the systems further include: a beta-lactone source to output at least one beta-lactone reagent to the at least one reaction vessel.

The reactor systems and processes for producing at least one organic acid product from at least one beta-lactone reagent use at least one heterogeneous catalyst such as zeolite, metal oxide, supported acid such as phosphoric acid (solid phosphoric acid—SPA), and/or heteropolyacid. In certain preferred embodiments, the at least one heterogeneous catalyst comprises silica-alumina molecular sieves, particularly those modified with phosphate compounds. Catalysts of the type that are specifically suited for this invention include alkaline-earth phosphates, supported phosphate salts, calcium hydroxyapatites, inorganic salts, metal oxides, and zeolites. In preferred embodiments, the at least one heterogeneous catalyst is an alumina-silicate molecular sieve and more preferably a zeolite having Lewis or Brönsted acidity. The zeolites can be in hydrogen form or in cation exchanged form. Suitable cations are alkali metals such as $Na^+$ or $K^+$; alkali-earth cations such as $Ca^{2+}$, $Mg^{2+}$, $Sr^{2+}$, or $Ba^{2+}$; as well as $Zn^{2+}$, $Cu^+$, and $Cu^{2+}$.

In certain preferred embodiments, the at least one heterogenous catalyst comprises zeolite catalysts chosen from a broad range of zeolites including zeolite framework types which may be beneficially used to practice this invention. The different zeolite framework types that may be most beneficially used in this invention comprise MFI (pentasil), FAU (faujasite), MAU (mordenite), BEA (beta) and MWW zeolite structures. Useful zeolites from these classes may comprise one-dimensional (1D: ZSM-22), two-dimensional (2D: MCM-22 and ZSM-35), or three dimensional (3D: ZSM-5, ZSM-11, ZSM-5/ZSM-11, and β-crystalline configurations. In some embodiments, the zeolites include ZSM-5, zeolite beta, zeolite Y, and zeolite A. In some embodiments, the zeolite has a micropore volume of at least 30%. In some embodiments, the zeolite has a micropore volume in the range of between 30% and 80%, or between 60% and 80%. In some embodiments, the zeolite is a ZSM-5 zeolite or a Y zeolite having a micropore volume in a range between 30% and 45%.

In certain embodiments, the heterogenous catalyst is preferably a sodium form ZSM-5 or beta zeolite that an at least 50%, at least 70% or at least 90% exchange of potassium cations with the available cation exchange sites. In certain embodiments, the at least one heterogenous catalyst is preferably a sodium form ZSM-5 that has an at least 50%, at least 70% or at least 90% exchange of potassium cations with the available cation exchange sites and a $SiO_2/Al_2O_3$ ratio in a range of between 20 and 120, of between 20 and 50 or between 20 and 30.

In certain preferred embodiments of the present invention, the beta-lactone reagents may have a high bio content comprised of carbon atoms from biological sources, recycled sources, renewable sources, and/or otherwise sustainable sources. Such sources may include crop residues, wood residues, grasses, municipal solid waste and algae. In some embodiments, the beta-lactone reagents may be comprised of carbons from any source.

Below is anon-exhaustive list of beta-lactone reagents which may undergo a single step reaction to produce at least one organic acid product.

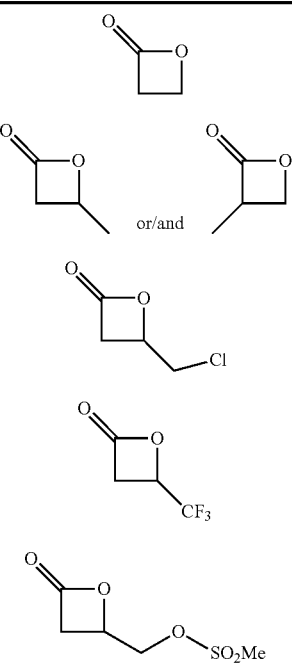

-continued
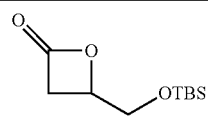
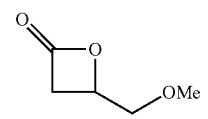
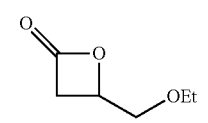
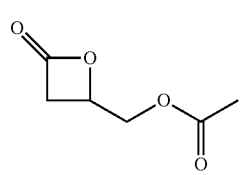
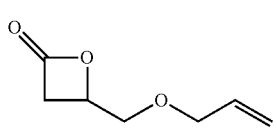
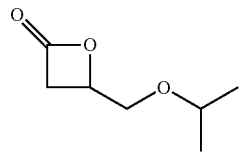
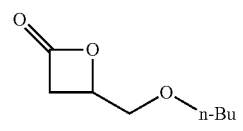
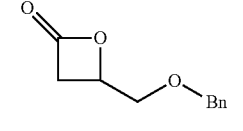 [SMILES: O=C1CC(COCc2ccccc2)O1]
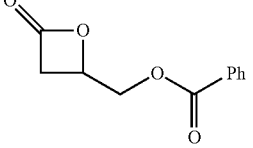
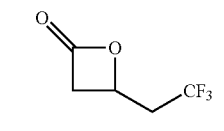
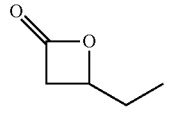
-continued
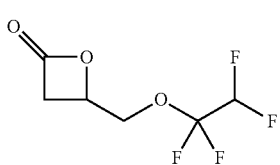 [SMILES: O=C1CC(COC(F)(F)C(F)F)O1]
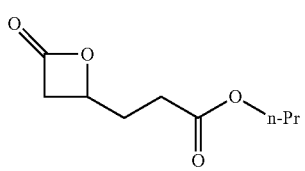
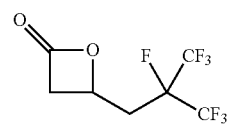
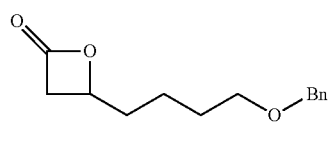 [SMILES: O=C1CC(CCCCOCc2ccccc2)O1]
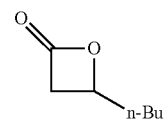
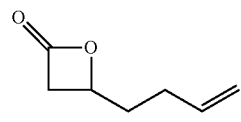
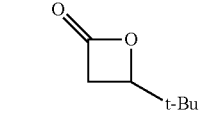
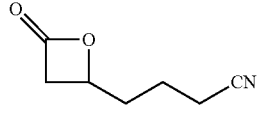
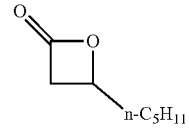
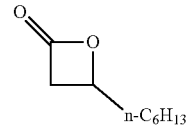

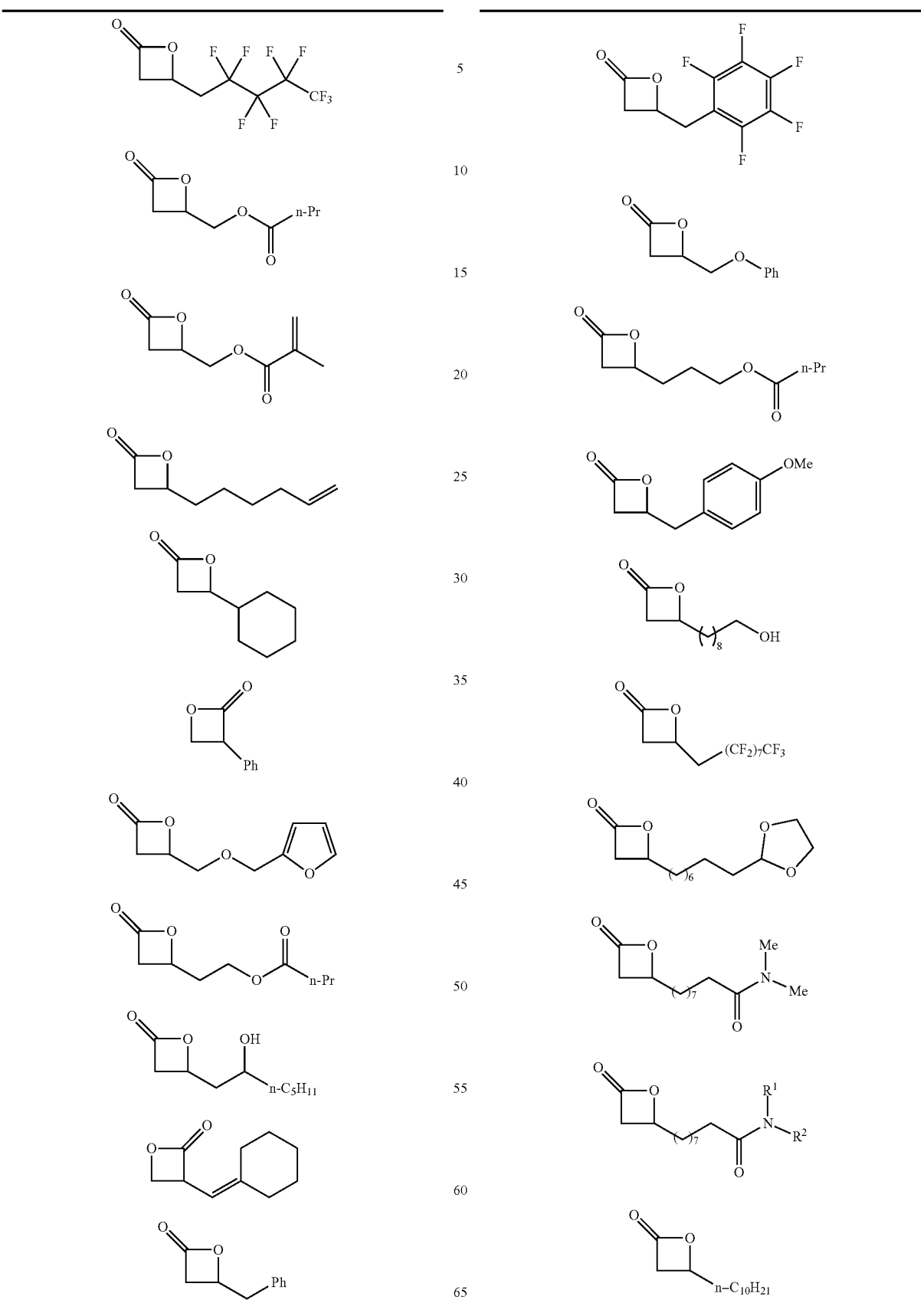

-continued

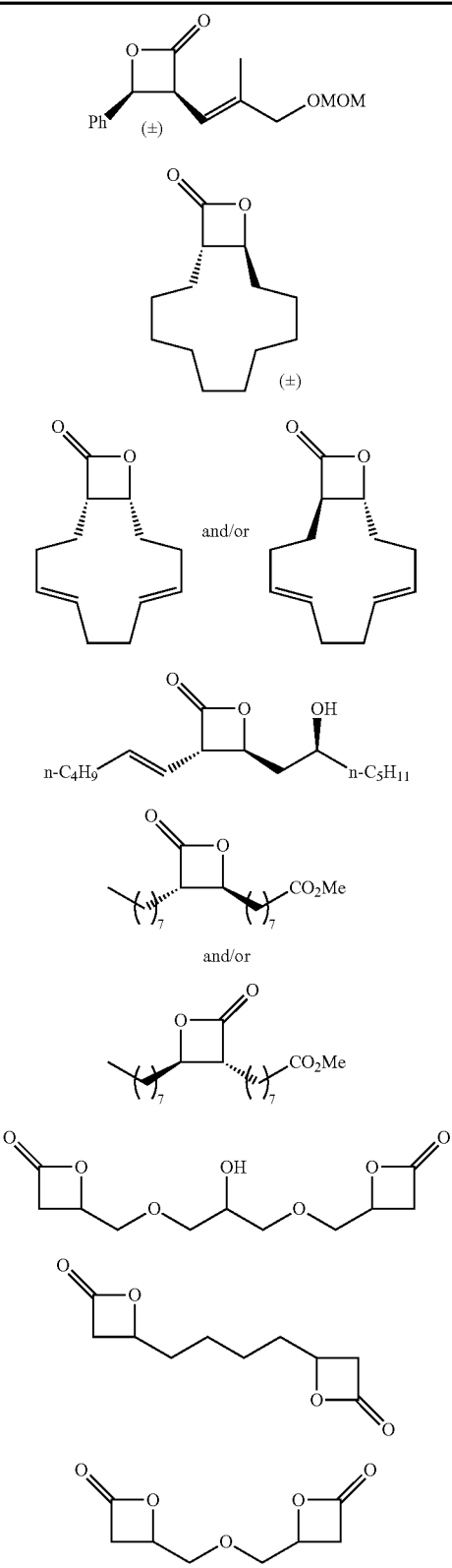

In certain preferred embodiments, the reactor systems and processes may include at least one reaction vessel comprising a continuous fixed-bed reactor operating at a reduced pressure for production of at least one organic acid product. In certain embodiments, the continuous fixed-bed reactor is operated at the pressure between 40 Torr and 250 Torr. At least one beta-lactone reagent may be introduced to the continuous fixed-bed reactor through at least one feed stream inlet while in vapor phase. In certain embodiments, the at least one beta-lactone reagent is vaporized at the temperature between 80° C. and 127° C. and then introduced to the at least one feed stream inlet of the continuous fixed-bed reactor packed with a heterogenous catalyst. The continuous fixed-bed reactor is operated in the temperature range from 100° C. to 300° C., and preferably from 150° C. to 250° C.

In certain preferred embodiments, the reactor systems and processes may include at least one reaction vessel comprising a continuous fixed-bed reactor configured for receiving at least one beta-lactone reagent diluted with inert solvent or gas. The inert solvent or gas may be hexane, nitrogen, argon, or helium. The continuous fixed-bed reactor may operate at atmospheric pressure, at the pressure below atmospheric pressure, or at the pressure above atmospheric pressure. In some embodiments, the continuous fixed-bed reactor is operated the pressure between 250 Torr and 50 psig. In certain preferred embodiments, the continuous fixed-bed reactor is operated at the pressure from 5 psig to 30 psig and temperature range from 100° C. to 300° C., or more preferably from 150° C. to 250° C.

In certain preferred embodiments, the at least beta-lactone reagent is introduced to the reactor in the flow of nitrogen or another inert gas. In some variations, the weight ratio of the at least one beta-lactone reagent to inert gas is from 0.05:1 to about 1.5:1. In some embodiments, the inert gas is introduced to the continuous fixed-bed reactor containing the at least one beta-lactone reagent in the liquid phase and maintained at the temperature required to achieve the desired concentration of the at least one beta-lactone reagent in the inert gas. Then the mixture of the at least one beta-lactone reagent and inert gas is introduced through the feed stream inlet of the continuous fixed-bed reactor. In other embodiments, the at least one beta-lactone reagent is injected into a stream of inert gas near and then introduced through inlet of the continuous fixed-bed reactor. In preferred embodiments, the concentration of the at least one beta-lactone reagent in inert solution or gas is from 10% to 99%.

In certain preferred embodiments, the conversion of the at least one beta-lactone reagent to the at least one organic acid product is performed in the presence of a solvent or diluent. In some embodiments, the solvent or diluent selected (i) dissolves, or at least partially dissolves, the at least one beta-lactone reagent, but does not react, or minimally reacts, with the at least one beta-lactone reagent; or (ii) has a high boiling point so that the at least one organic acid product may be distilled while solvent remains in a reaction vessel, or a combination of (i) and (ii). In some embodiments, the solvent is a polar aprotic solvent. For example, the solvent may be a high boiling polar aprotic solvent. In one variation, the solvent includes sulfolane. In some embodiments, the at least one beta-lactone reagent may be diluted in solvent at the ratio of about 1:1. The solvent may be dried using any suitable methods or techniques known in the art prior to use. A combination of any of the solvents described herein may also be used.

In certain preferred embodiments, the reactor systems and processes of the present invention may include at least one reaction vessel configured to have more than one section and heat exchangers installed between sections. In certain embodiments, the reactor systems include at least one reaction vessel are configured to have more than one section, all the at least one beta-lactone reagent is converted inside the at least one reaction vessel with the selectivity to at least one organic acid product greater than 90% and preferably greater than 95% and most preferably greater than 99%. In other embodiments, only part of the at least one beta-lactone reagent is converted to at least one organic acid product and another part of the at least one beta-lactone reagent exiting the at least one reaction vessel is left unconverted. In certain embodiments, the unconverted at least one beta-lactone reagent can be recovered and recycled back to the feed stream inlet of one or more sections of the reaction vessel and/or one or more other reaction vessels. The at least one beta-lactone reagent in certain embodiments comprising at least one reaction vessel configured to have more than one section and heat exchangers installed between sections is greater than 50%, preferably, greater than 75%, and most preferably greater than 80% and the residence time in one or more reaction vessels is in the range from 0.1 second to 2 minutes.

In certain preferred embodiments, the reactor systems and processes may include at least one reaction vessel configured as a tubular shell-and-tube reactor with a heterogenous catalyst loaded into the tubes and heat transfer fluid fed to the shell side to facilitate temperature control and removal of the heat produced during the reactions. In certain embodiments, the tubular shell-and-tube reactor may be configured as a sectioned tubular shell-and-tube reactor comprising more than one section with heat exchangers installed between sections. In certain preferred embodiments, all the at least one beta-lactone reagent is converted inside the sectioned tubular shell-and-tube reactor with the selectivity to at least one organic acid product greater that 90%, preferably greater than 95%, and most preferably greater than 99%. In certain embodiments, only part of the at least one beta-lactone reagent in the sectioned tubular shell-and-tube reactor is converted to the at least one organic acid product and another part of the at least one beta-lactone reagent exits the sectioned tubular shell-and-tube reactor unconverted. In some embodiments, any unconverted at least one beta-lactone reagent can be recovered and recycled back through a feed stream inlet of the sectioned tubular shell-and-tube reactor. In some embodiments, the residence time in the sectioned tubular shell-and-tube reactor is in the range from 0.1 second to 2 minutes.

In some embodiments, a polymerization inhibitor is used in the conversion of the at least one beta-lactone reagent to at least one organic acid. In some embodiments, the polymerization inhibitor may be a radical polymerization inhibitor, for example, phenothiazine.

Figure 2:
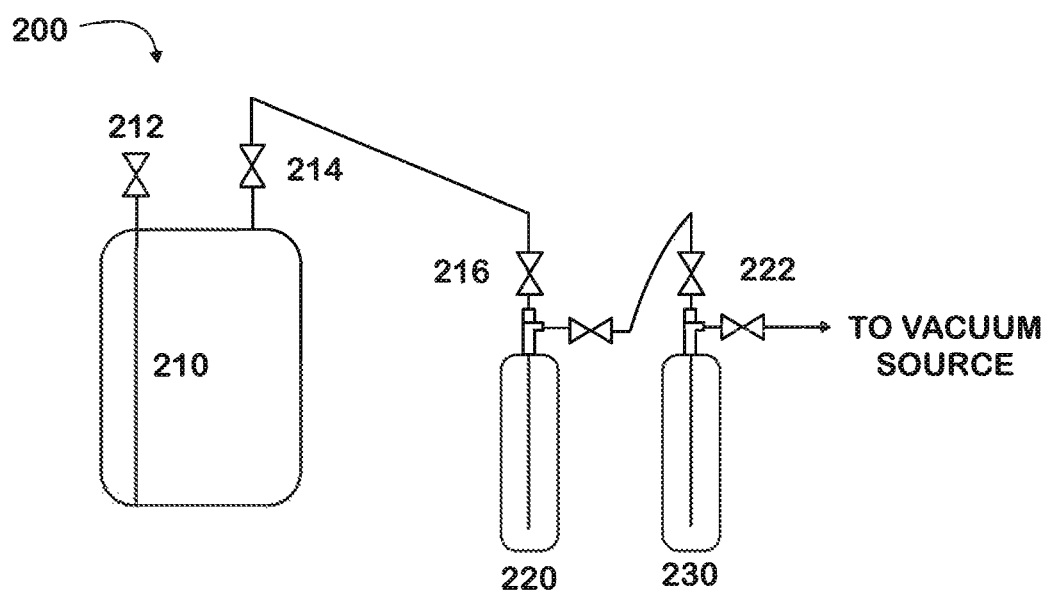
FIG. 2 depicts an exemplary reaction system to produce an organic acid product from a beta-lactone reagent according to the processes described herein.

FIG. 2 illustrates an exemplary embodiment of a reactor system 200 including a reaction vessel 210 defining an interior volume configured to receive a beta-propiolactone reagent, a zeolite heterogenous catalyst, and a polymerization inhibitor. The reaction vessel 210 defines a retaining volume to retain the beta-propiolactone reagent, the zeolite heterogenous catalyst, and the polymerization inhibitor and is configured to produce acrylic acid at an elevated temperature. Any of the temperatures described for the processes of the present invention may be employed in the reactor system 200. For example, in one variation, the reaction vessel 210 is configured to produce an organic acid at a temperature between 170° C. and 200° C. Suitable reaction vessels may include, for example, a Parr reactor.

In some variations, reaction vessel 210 is configured to control the rate of addition of the beta-propiolactone reagent, the zeolite heterogenous catalyst, and the polymerization inhibitor added. For example, a mixture of the beta-propiolactone reagent and the polymerization inhibitor may be slowly added using a control valve to a mixture of catalyst in a solvent.

With reference again to FIG. 2, reaction vessel 210 further includes vapor port 214. In some embodiments, the reaction vessel 210 is configured to continuously strip off at least a portion of the organic acid produced, and vapor port 214 is configured to pass organic acid vapors to a collection vessel 220.

With reference again to FIG. 2, the reactor system 200 further includes an acid/base scrubber 230, configured to receive organic acid from the collection vessel 220. In other embodiments of the reactor system, the acid/base scrubber 230 may be omitted. Further, with reference to FIG. 2, elements 212, 216 and 222 are dip tubes.

Figure 3:
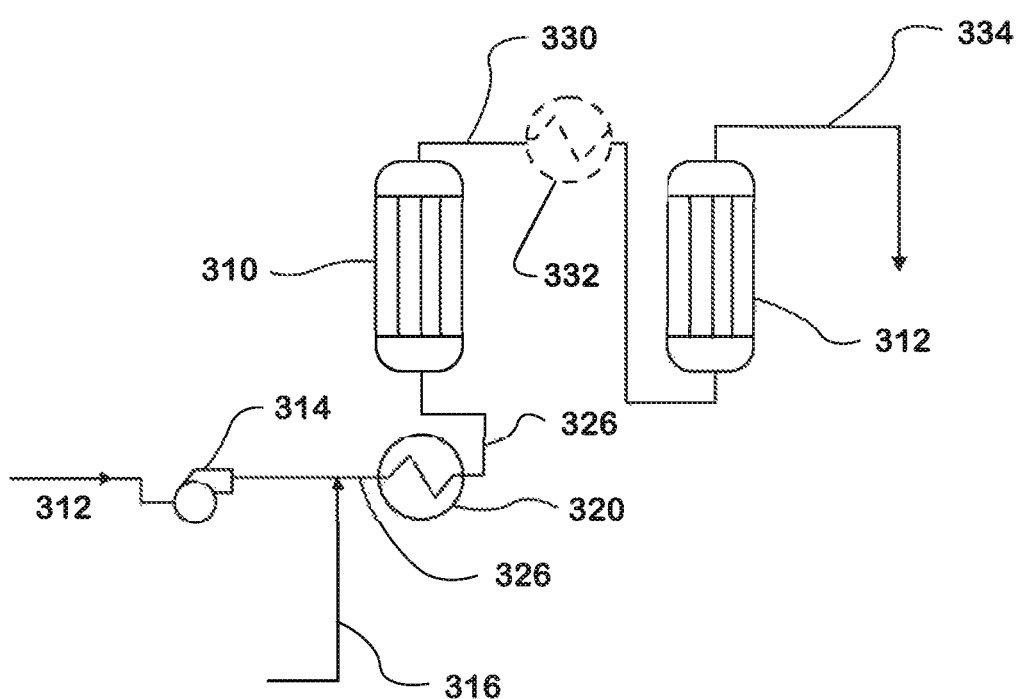
FIG. 3 is a process flow diagram for a fixed bed operation of the reactor system to produce an organic acid product directly from a beta-lactone reagent according to the processes of this invention.

FIG. 3 illustrates a reactor system including at least one reaction vessel comprising a fixed-bed reactor. In FIG. 3, a beta-propiolactone reagent may optionally be admixed with a solvent and enter the reactor system via a feed line 312. A pair of fixed-bed reactors 310 and 313 each retaining multiple tubular beds of catalyst are configured to receive beta-propiolactone reagent from the feed line 312 at rate controlled by a feed pump 314 to control the rate of addition of the beta-propiolactone reagent. The tubular form of fixed-bed reactor is preferred for removing heat from the catalyst bed during the reaction, but is not required and other types of fixed-bed reactors and arrangements may be used. The depiction of two reactors is for illustration purposes only and the process may use a single fixed-bed reactor or any number of fixed-bed reactors. Input line 316 may optionally supply additional process input streams such as diluents into admixture with the contents of line 324 to produce a reactor input stream 326.

The reactor input stream 326 undergoes heating to produce a vapor phase feed stream. A heat exchanger 320 supplies a heat input to reactor input stream 326. Heat may be from an internal process stream or from an external heat source. The heating will be sufficient to ensure that the reactor input stream is in a complete vapor phase before it enters fixed-bed reactor 310.

The beta-propiolactone reagent is converted at least in part to organic acid in fixed-bed reactor 310 and fixed-bed reactor 312. A transfer line 330 passes an intermediate stream containing unconverted beta-propiolactone reagent and organic acid along with any additional input materials added with the beta-propiolactone reagent to fixed-bed reactor 312. An optional heat exchanger 332 may be added to control and adjust, typically by heat removal, the temperature of the intermediate stream before it enters fixed-bed reactor 312. An effluent stream 334 is recovered from fixed-bed reactor 312. Reactor effluent stream 334 contains any unconverted beta-propiolactone reagent, organic acid and any additional input materials that may have been added to the reactor input stream 326.

Typically, a product separation section (not shown) receives effluent stream 334 to recover the organic acid product. Along with recovery of the organic acid product the separation section will in most cases also recover unconverted beta-propiolactone reagent (which is usually recycle) and the diluent and the other additive streams that may have been added with the feed and are still recoverable while also rejecting unwanted by-products.

Figure 4:
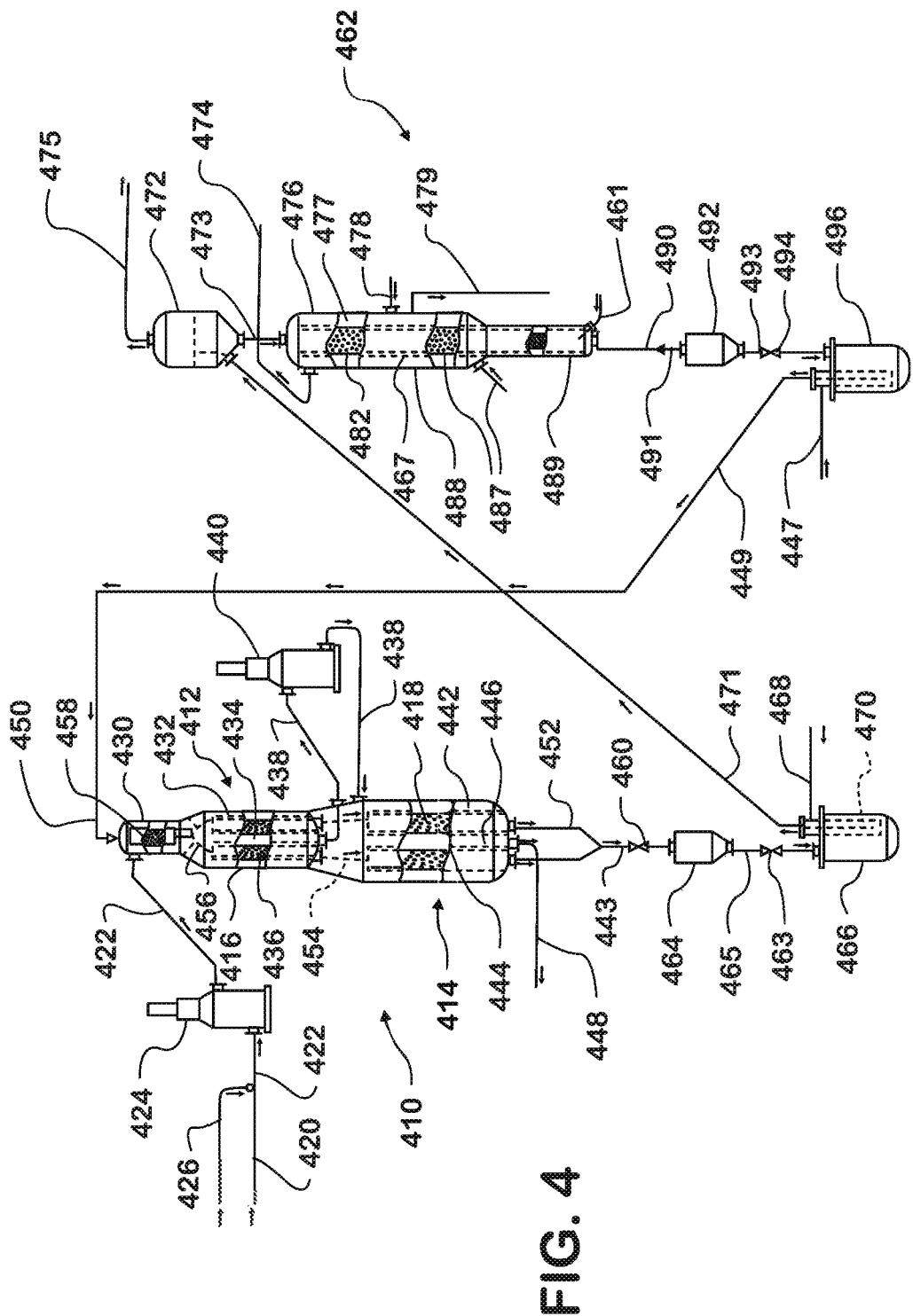
FIG. 4 is a process flow diagram for a moving bed operation of the reactor system to produce an organic acid product directly from a beta-lactone reagent according to the processes of this invention.

FIG. 4 illustrates a reactor system including at least one reaction vessel comprising a moving bed reactor. More specifically, FIG. 4 illustrates a reaction vessel 410 which defines an upper reaction section 412 that holds a bed of heterogenous catalyst 416 and a lower reaction section 414 that holds a bed of heterogenous catalyst 418, with both moving bed reactor beds arranged for radial flow of reactants across each of the reaction sections.

With respect to fluid flow, reactor vessel 410 is configured to receive a combined beta-propiolactone reagent feed stream comprising the beta-propiolactone reagent. A feed line 420 delivers the beta-propiolactone reagent and an additive line 426 delivers any additives for combination into a combined feed 422 that passes through a heater 424 configured for heating the combined feed to ensure delivery of an all vapor phase combined feed stream to reactor section 412. The combined feed passes through a heat exchange vessel 430 that is provided to heat the heterogenous catalyst that is entering the moving bed reactor vessel 410 via a catalyst transfer line 450. The combined feed flows downward into an annular distribution space 432 that distributes it around the heterogenous catalyst bed 416. After the combined feed passes through bed 416 a center pipe 436 collects an upper reactor effluent comprising acrylic acid, unreacted combined feed and any remaining additives for transfer from the vessel into an inter-heater 440 via a line 438. An inter-heater 440 raises the temperature of the first reactor section effluent and returns the heated upper reactor effluent passes to the lower reactor section 414 via line 428. An annular space 442 distributes the heated upper reactor effluent around the lower heterogenous catalyst bed 418. A lower reactor effluent passes through a center pipe 444 and into annular space 446. A line 448 recovers the lower reactor effluent and passes it similar to recovery of acrylic acid product and optional recycle of unconverted beta-propiolactone reagent, recovery of additives, and removal of by-products.

In FIG. 4, the heterogenous catalyst is periodically removed from the bottom of the reaction vessel 410 by a catalyst removal line 443 and replaced at the top of the reaction vessel 410 by a catalyst transfer line 450. The heterogenous catalyst flows through the reaction vessel by dropping from a catalyst flow line 460 and from collection pipes 452 that withdraw heterogenous catalyst from the annular catalyst bed 418. As catalyst drops from the bed of heterogenous catalyst 412, transfer pipes 454 add heterogenous catalyst from the bed of heterogenous catalyst 416 and distribute the heterogenous catalyst around the bed of heterogenous catalyst 418. In turn, as heterogenous catalyst drops from the bed of heterogenous catalyst 416, transfer pipes 456 replace it with heterogenous catalyst withdrawn from heat exchange section 458 of heat exchanger 430 that receives fresh and/or regenerated catalyst from catalyst transfer line 450.

In certain embodiments, the reaction vessel 410 may operate with or without continuous regeneration. In the latter case, deactivated or partially deactivated catalyst withdrawn by the catalyst flow line 460 may be discarded or transferred to remote regeneration facilities located on-site or off-site for reactivation and reuse of the spent catalyst. The catalyst transfer line 450 will be used to supply reactivated or fresh catalyst to the moving bed reactor vessel 410 as catalyst is withdrawn vial catalyst flow line 460.

FIG. 4 illustrates regeneration system 462 that receives at least partially deactivated catalyst from reaction vessel 420 via a reactivated catalyst line 471 and returns reactivated, and optionally treated catalyst to moving bed reactor vessel 410 via the catalyst transfer line 450. The transfer of catalyst to the regeneration system 462 begins with the intermittent passage of catalyst to a lock hopper 464 through line 443 upon the opening and closing of an upper control valve. Another control valve 463 regulates the movement of catalyst from lock hopper 464 into a lift vessel 466. When heterogenous catalyst is ready for regeneration transfer through reactivated catalyst line 471, control valve 463 is closed and lift gas enters lift vessel 470 via line 468 and is carried to the bottom of lift vessel 466 by lift gas tube 470. The lift gas carries the catalyst upward into a catalyst hopper 472 of regeneration system 462. Lift gas disengages from the catalyst in vessel 472 and is removed from the regeneration section 479 by conduit 475.

Heterogenous catalyst is regenerated as it flows intermittently from the top to the bottom of regeneration system 462. Intermittent passage of catalyst begins with the opening of a valve 490 in a line 491 that results in catalyst from hopper 472 passing downwardly through a line 473 into an upper chamber 477 of a combustion vessel 476 as catalyst drops into a lower portion 488 of the combustion vessel 476 to replace catalyst the dropped into a lock hopper 492. Valve 491 isolates lock hopper 492 for transfer of catalyst into lift vessel 496. Catalyst is transported from lift vessel 496 into line 450 by closing valve 494 and injecting lift gas into lift vessel 496 via line 447 in the manner previously described.

In certain embodiments, the regeneration system passes a regeneration gas and may optionally pass one or more treatment and/or purge gases through the regeneration section. A baffle 467 divides the combustion vessel into the upper chamber 477 and the lower chamber 488. The primary regeneration gas enters the regeneration section 462 via a line 478 and passes into the bottom of upper chamber 477, across a bed 482 of deactivation catalyst. A line 474 withdraws the regeneration gas from the top of upper chamber 477. Additional regeneration gas or treatment gas enter the bottom of lower chamber 488 via line 487. An additional gas stream, typically a treatment gas may also enter a lower contact zone 489 via a line 461. A line 479 withdraws gas from lower chamber 488 below baffle 467. Since lower contact zone 489 communicates with combustion vessel 476 conduit 479 also withdraws gas that enter the lower contact zone 489.

In certain preferred embodiments, the reactor systems and processes of the present invention include at least one reaction vessel comprising a fluidized bed reactor configured to receive at least one beta-lactone reagent diluted with inert gas such as nitrogen. The fluidized bed reactor includes at least one reaction zone where the heterogenous catalyst is suspended/fluidized in the flow of an inert gas such as nitrogen. The fluidized-bed reactor may operate at atmospheric pressure, at the pressure below atmospheric pressure, or at the pressure above atmospheric pressure. In certain embodiments, the fluidized-bed reactor operates at a pressure between 250 Torr and 50 psig, but preferably from 5 psig to 30 psig. In certain embodiments, the fluidized-bed reactor is operated in the temperature range from 100° C. to 300° C., and preferably from 150° C. to 250° C. Inert gas such as nitrogen is introduced to the fluidized-bed reactor to fluidize the heterogenous catalyst. The temperature of the gas entering the fluidized-bed reactor can be adjusted to maintain the reactor at the desired temperature. In preferred embodiments, the at least one beta-lactone reagent is introduced through at least one feed stream inlet at the bottom of the fluidized-bed reactor and the at least one organic acid product, by-products, and inert gas exit from the top of the fluidized-bed reactor. In some embodiments, the inert gas is separated from the at least one organic acid product and recycled to the at least one feed stream inlet of the fluidized-bed reactor. In some embodiments, the fluidized-bed reactor can be configured to include a regeneration zone where the heterogenous catalyst may be regenerated to be reused in subsequent reactions. The heterogenous catalyst can be regenerated in a flow of air or dilute oxygen to remove deposited coke. In some embodiments, deactivation of the heterogenous catalyst may occur over time from at least one of organic material depositing on the surface of the heterogenous catalyst and the production of coke within the pores and on the surface of the zeolite and/or the accumulation of polar acidic compounds. The composition of the heterogenous catalyst along with operating conditions, primarily temperature will determine the rate of heterogenous catalyst deactivation by coke formation. Removal of coke and organic material by combustion at elevated temperatures may be incorporated to effectively restore the activity of the heterogenous catalyst. Regeneration will typically occur at a temperature of 450° C. or higher. Preferably regeneration will be in a range of between 450° C. and 550° C.

Figure 5:
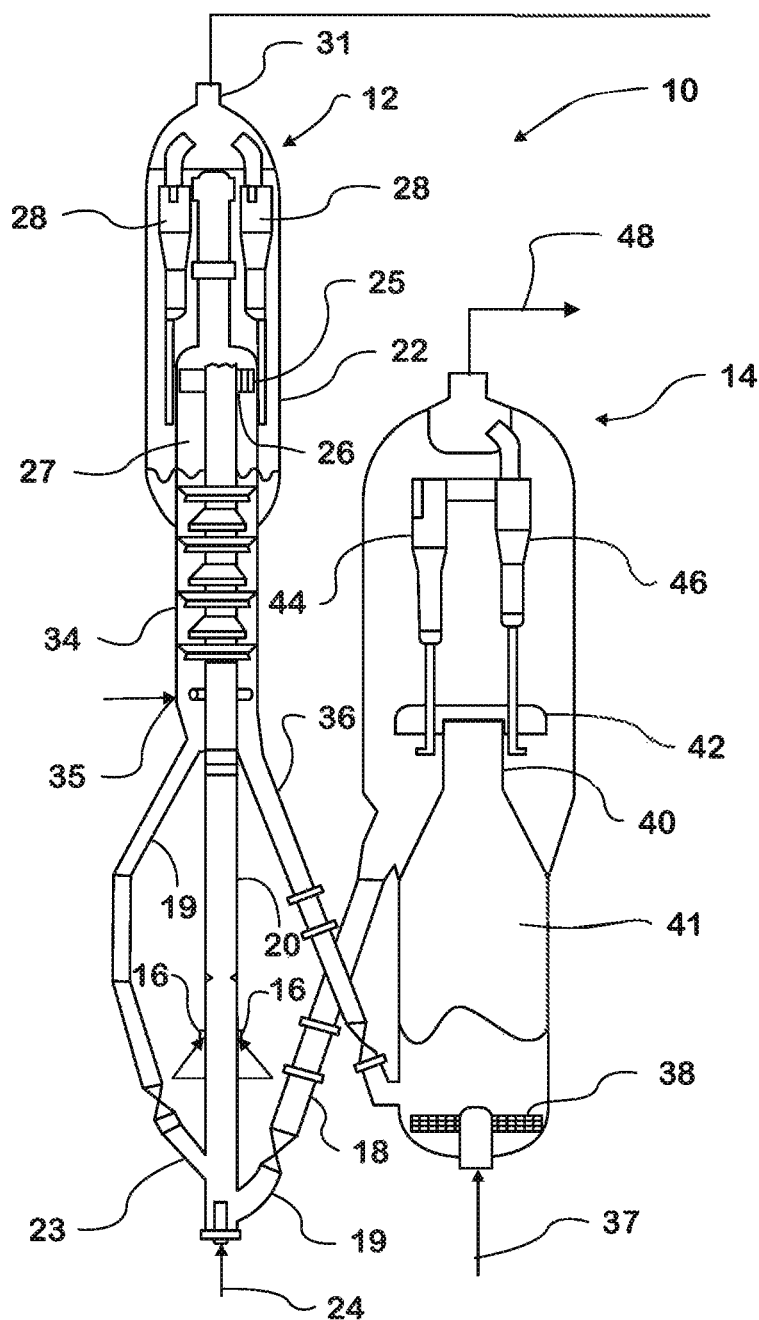
FIG. 5 is a process flow diagram for a fluidized bed operation of the reactor system to produce an organic acid product directly from a beta-lactone reagent according to the processes of this invention.

FIG. 5 illustrates a reactor system including at least one reaction vessel comprising a fluidized bed reactor 10. FIG. 5 shows a fluidized bed reactor 10 that includes a dilute phase transfer zone as the catalyst contact zone which may be referred to as riser 20. The fluidized bed reactor 10 is configured for fluidized catalyst contacting a beta-propiolactone reagent in a reaction zone 12. In the fluidized bed reactor 10 a beta-lactone feed stream is contacted in reaction zone 12 with a heterogenous catalyst. In certain embodiments, a regenerated heterogenous catalyst entering from a regenerator conduit 18 contacts the beta-lactone reagent combined feed stream comprising beta-lactone and one or more of diluents fluidization gases, and other additives as herein described. In certain preferred embodiments, the regenerated heterogenous catalyst is at substantially higher temperature than the combined feed and additional heating of the feed by contact with the regenerated heterogenous catalyst can provide additional fluidization to lift the heterogenous catalyst and carry up the riser 20 of the fluidized bed reactor 12. The regenerator conduit 18 is in downstream communication with the regenerator 14. The riser 20 has an inlet 19 in downstream communication with said regenerator conduit 18. The regenerator conduit 19 is connected to the FCC riser 20 at a lower end. A control valve located between sections 18 and 19 of the regenerator conduit regulates the flow of heterogenous catalyst out of the regenerated catalyst conduit and provides a pressure drop that prevents any substantial flow of the feed stream up the section 18 of the regeneration conduit.

In the FIG. 5 illustrated embodiment, spent cracking catalyst entering from a recycle catalyst conduit 19 and a riser inlet tube 23 is contacted with the combined beta-propiolactone feed stream riser 20 of the fluidized bed reactor 12 without the spent cracking catalyst undergoing regeneration. A valve at the top of riser inlet tube 23 regulates the flow of catalyst through the riser inlet tube 23. The spent cracking catalyst recycle will allow additional control of the temperature and/or the activity of the heterogenous catalyst in the fluidized bed reactor 12 and can increase the coke concentration of the heterogenous catalyst in the fluidized bed reactor 12 to aid in the regulation of regenerator temperatures and heterogenous catalyst regeneration.

The recycle of spent heterogenous catalyst through the recycle catalyst conduit can also be used to increase the ratio of catalyst-to-feed in the fluidized bed reactor. In some embodiments, the catalyst-to-feed weight ratio is in a range between 5 and 20 and preferably between 10 and 15. In some embodiments portions of the beta-propiolactone feed may be fed to the riser 20 through elevated distributors 16 and this can be used to maintain conversion of the beta-propiolactone reagent as the heterogenous catalyst passes up the riser 20.

The recycle conduit 19 is in downstream communication with a riser outlet 25. The recycle conduit 19 is connected to the riser 20 at the outlet end of the recycle conduit by riser tube 23. The recycle conduit 19 bypasses the regenerator 14 by being in downstream communication with the riser outlet 25 and the riser tube 23 being in direct, downstream communication with the recycle conduit. Consequently, spent cracking catalyst entering the recycle conduit 19 passes back to the riser 20 before any of it enters the regenerator 14. The recycle conduit 19 has no direct communication with the regenerator 14.

The organic acid containing product gases and spent heterogenous catalyst in the riser 20 are thereafter discharged from the riser outlet 25 into a disengaging chamber 27 which contains the riser outlet. The gas stream containing acrylic acid product is disengaged from the heterogenous catalyst in the disengaging chamber 27 using a rough cut separator 26. Cyclonic separators which may include one or two stages of cyclones 28 in the fluidized bed reactor reaction chamber 22 further separate heterogenous catalyst from organic acid products. Product containing gases exit the fluidized bed reactor reaction chamber 22 through an outlet 31 for transport to downstream product separation facilities to recover acrylic acid, recycle beta-propiolactone reagents, diluents and additives. In another embodiment, the recycle conduit 19 and the regenerator conduit 18 are in downstream communication with the disengaging chamber 27. The outlet temperature of the product containing gas leaving the riser 20 should be less than 325° C. and preferably less than less than 300° C.

After separation from product containing gases, the heterogenous catalyst falls into a stripping section 34 where an inert gas is injected through a nozzle 35 and distributed to purge any residual product vapor or gas. After the stripping operation, a portion of the spent cracking catalyst is fed to the catalyst regenerator 14 through a spent catalyst conduit 36. The catalyst regenerator 14 may be in downstream communication with the riser 20, specifically, the riser outlet 25. In certain embodiments, a portion of the spent heterogenous catalyst is recycled through recycle catalyst conduit 19 to the riser 20 as previously described.

The flue gas will typically contain carbon dioxide, water vapor, and lesser amounts of carbon monoxide. Depending on the type and the erosion properties of the catalyst the flue gas may also contain small amounts of extremely fine catalyst particles typically in the range of between 0.2 and 2 micrometers which in some applications will require additional treatment of the flue gas for removal of such particles.

FIG. 5 depicts a regeneration vessel 14 for the regeneration of heterogenous catalyst having a combustor 41 as the primary zone for the regeneration of the heterogenous catalyst by combustion of the coke and the displacement of other volatile compounds from the surface of the spent cracking catalyst. Other embodiments of the invention may use other configurations and arrangement of regenerators. In the regeneration vessel 14, a stream of oxygen-containing gas, such as air, is introduced from line 37 through a distributor 38 to contact the coked catalyst, burn coke deposited thereon, and provide regenerated catalyst and a gas stream comprising the products of the combustion and generally referred to as flue gas. Catalyst and air flow upwardly together through the combustor 41 and along a combustor riser 40 located within the regeneration vessel 14. The catalyst which is at least partially regenerated is discharged through a disengager 42 to effect an initial separation of the catalyst from the flue gas. A series of cyclonic separation steps in cyclones 44 and 46 effect further separation of regenerated catalyst and flue gas. The cyclones direct the catalyst separated therein into the conduits that extend downwardly from the cyclones and are referred to as diplegs. The flue gas which is relatively free of catalyst exits cyclones 44, 46 and flows out of the regenerator vessel 14 through line 48. Regenerated heterogenous catalyst is recycled back to the reactor riser 20 through the regenerated catalyst conduit 18.

Enumerated Embodiments

The following enumerated embodiments are representative of some aspects of the invention.

1. A process for producing at least one organic acid product directly from at least one beta-lactone reagent, wherein the at least one beta-lactone reagent is represented by the following formula:

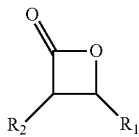

wherein $R_1$ and $R_2$ are independently selected from the group consisting of H, alkyl, alkenyl, alkoxy, alkyryl, cycloalkyl, cycloalkenyl and cycloalkynyl, wherein both of $R_1$ and $R_2$ are not H at the same time, comprising the steps: introducing at least one beta-lactone reagent to at least one reaction vessel; contacting the at least one beta-lactone reagent with at least one heterogenous catalyst in the at least one reaction vessel to produce at least one organic acid; and removing the at least one organic acid from the at least one reaction vessel to provide at least one organic acid product.

2. The process from embodiment 1, wherein the heterogenous catalyst comprises a microporous solid selected from the group including alkaline-earth phosphates, supported phosphate salts, calcium hydroxyapatites, inorganic salts, metal oxides, and zeolites, or combinations thereof.

3. The process from embodiment 1, wherein the heterogenous catalyst comprises an alumina-silicate molecular sieve having Lewis or Brönsted acidity.

4. The process from embodiment 1, wherein the heterogenous catalyst comprises a zeolite.

5. The process from embodiment 4, wherein the heterogenous catalyst comprises Zeolite Y, beta Zeolite, ZSM-5, ZSM-11 ZSM-22, MCM-22, ZSM-35, Zeolite A, or combinations thereof.

6. The process from embodiment 2, wherein the zeolite catalyst is in a hydrogen form or in metal cation exchanged form 7. The process from embodiment 6, wherein the metal cations are $Na^+$, $K^+$, $Ca^{2+}$, $Mg^{2+}$, $Cu^{2+}$, $Cu^+$.

8. The process from embodiment 1, wherein the at least one organic acid product is produced continuously.

9. The process from embodiment 1, wherein the at least one beta-lactone reagent is introduced to the at least one reaction vessel combined with a solvent.

10. The process from embodiment 1, wherein the at least one reaction vessel further comprises a continuous fixed-bed reactor operating at a reduced pressure.

11. The process from embodiment 1, wherein the at least one reaction vessel further comprises a continuous fixed-bed reactor configured for receiving at least one beta-lactone reagent diluted with inert gas 12. The process from embodiment 1, wherein the least one reaction vessel further comprises a fluidized bed reactor configured to receive at least one beta-lactone reagent diluted with inert gas such as nitrogen.

13. The process from embodiment 1, wherein the least one reaction vessel further comprises a tubular shell-and-tube reactor with a heterogenous catalyst loaded into the tubes and heat transfer fluid fed to the shell side to facilitate temperature control and removal of the heat produced during the reactions.

14. The process from embodiment 1, wherein the beta-lactone reagent is provided at a weight hourly space velocity of $0.1\ h^{-1}$ to $2.1\ h^{-1}$.

15. The process from embodiment 1, wherein the beta-lactone reagent is provided at a weight hourly space velocity of $0.3\ h^{-1}$ to $0.9\ h^{-1}$.

16. The process from embodiment 1, wherein the at least one organic acid product is continuously isolated.

17. The process from embodiment 1, wherein the at least one organic acid product is produced at a yield of at least 50%.

18. The process from embodiment 1, wherein the at least one organic acid product is produced at a temperature between 100° C. and 300° C.

19. A reactor system for producing at least one organic acid product directly from at least one beta-lactone reagent, wherein the at least one beta-lactone reagent is represented by the following formula:

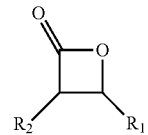

wherein $R_1$ and $R_2$ are independently selected from the group consisting of H, alkyl, alkenyl, alkoxy, alkynyl, cycloalkyl, cycloalkenyl and cycloalkynyl, wherein both of $R_1$ and $R_2$ are not H at the same time, wherein the reactor system comprises: at least one reaction vessel configured as a continuous fixed-bed reactor or a fluidized bed reactor defining at least one feed stream inlet and at least one product stream outlet; said at least one reaction vessel further defining an interior volume for receiving the at least one beta-lactone reagent from said at least one feed stream inlet and a retaining volume adapted for retaining the at least one beta-lactone reagent in solid, liquid, and gaseous phases.

20. The reactor from embodiment 19, wherein the at least one reaction vessel further comprises a fixed-bed reactor.

21. The reactor system from embodiment 19, wherein the at least one reaction vessel further comprises a continuous fixed-bed reactor operating at a reduced pressure for production of at least one organic acid product.

22. The reactor system from embodiment 19, wherein the at least one reaction vessel further comprises a continuous fixed-bed reactor configured for receiving at least one beta-lactone reagent diluted with inert solvent or gas.

23. The reactor system from embodiment 19, wherein the at least one reaction vessel further comprises a fluidized bed reactor configured to receive at least one beta-lactone reagent diluted with inert gas.

24. The reactor system from embodiment 19, wherein the at least one reaction vessel further comprises two or more sections separated by one or more heaters.

25. The reactor system from embodiment 19, wherein the at least one reaction vessel further comprises a tubular shell-and-tube reactor with a heterogenous catalyst loaded into the tubes and heat transfer fluid fed to the shell side to facilitate temperature control and removal of the heat produced during the reactions.

26. The reactor system from embodiment 19, wherein the at least one reaction vessel further comprises a regeneration vessel for the regeneration of at least one heterogenous catalyst.

EXAMPLES

The following Examples are merely illustrative and are not meant to limit any aspects of the present disclosure in any way.

Example 1

Conversion of β-methyl-β-propiolactone to trans-2-butenoic acid using a zeolite

This Example describes the production of trans-2-butenoic acid from the beta-propiolactone reagent exemplified below using a zeolite.

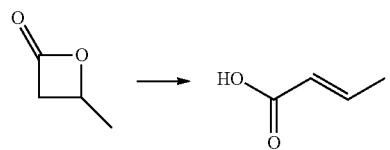

(1)

A mixture of β-methyl-β-propiolactone (3.0 g) and phenothiazine (9.0 mg) is added using a needle valve to a mixture of sulfolane (40.0 g) and Zeolite Y hydrogen (20.0 g) at about 165° C. with 50 psi of carbononoxide. Zeolite Y hydrogen (80:1 mole ratio $SiO_2/Al_2O_3$, powder S.A. 780 $m^2/g$) is dried under vacuum at about 100° C. for one day before use. Phenothiazine is the polymerization inhibitor used. Sulfolane is the solvent used, and is dried over 3 Å molecular sieves prior to use. β-methyl-β-propiolactone is added slowly using the needle valve over about 8.6 minutes. The reaction mixture is heated to about 170° C. to produce trans-2-butenoic acid.

The reaction is monitored by infrared spectroscopy (IR). The reaction is completed when no β-methyl-β-propiolactone is detectable by IR.

The zeolite is then filtered off from the reaction mixture, and a sample of the resulting mixture is dissolved in deuterium ($D_2O$) and chloroform ($CDCl_3$) for nuclear magnetic resonance (NMR) analysis.

Example 2

Vapor Phase Conversion of β-Methyl-β-Propiolactone to Trans-2-Butenoic Acid Using an H-ZSM-5

Vapor phase conversion of β-methyl-β-propiolactone to trans-2-butenoic acid is performed in packed-bed reactor using H-ZSM-5 (Si:Al=38, diameter 2 mm, surface area >=250 $m^2/g$) as a catalyst. 11 grams of H-ZSM-5 catalyst is loaded into jacketed stainless steel 316 pipe reactor (ID 0.5 inch), the catalyst is supported between glass beads columns (stainless steel wool is placed below and above glass beads). Multi-point thermocouple is inserted through the center of the reactor and hot oil is circulated through the reactor jacket to maintain the desired reactor temperature. β-methyl-β-propiolactone is fed to the reactor by means of saturator: $N_2$ at the rate of 28 g/hr is flown into the bottom of the vessel containing liquid β-methyl-β-propiolactone at a=94° C., this results in β-methyl-β-propiolactone feed rate of 5 g/hr. The pressure of reactor and saturator is maintained at 9.5 psig. The reaction products are chilled to about 10° C. dichloromethane, and the solution of reaction products in dichloromethane is analyzed by gas chromatography. The line between the saturator and the reactor as well as the line between the reactor and absorber are heat traced to prevent condensation of β-methyl-β-propiolactone to trans-2-butenoic acid. The reaction is conducted at the reactor temperature of about 210° C.

Example 3

Conversion of 3-Methyloxetan-2-One to Methacrylic Acid Using a Zeolite

This Example describes the production of methacrylic acid from 3-methyloxetan-2-one using a zeolite.

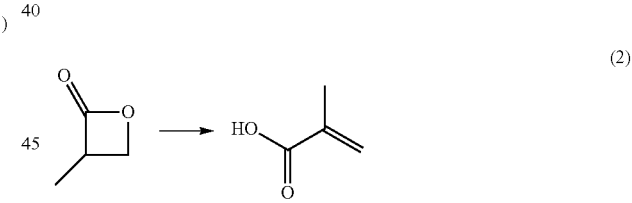

(2)

A mixture of 3-methyloxetan-2-one (3.0 g) and phenothiazine (9.0 mg) is added using a needle valve to a mixture of sulfolane (40.0 g) and Zeolite Y hydrogen (20.0 g) at 165° C. with 50 psi of carbon monoxide. Zeolite Y hydrogen (80:1 mole ratio $SiO_2/Al_2O_3$, powder S.A. 780 $m^2/g$) is dried under vacuum at 100° C. for one day before use. Phenothiazine is the polymerization inhibitor used. Sulfolane is the solvent used, and is dried over 3 Å molecular sieves prior to use. 3-methyloxetan-2-one is added slowly using the needle valve over about 8.6 minutes. The reaction mixture is heated to 170° C. to produce methacrylic acid.

The reaction is monitored by infrared spectroscopy (IR). The reaction is completed when no 3-methyloxetan-2-one is detectable by IR.

The zeolite is then filtered off from the reaction mixture, and a sample of the resulting mixture is dissolved in deuterium ($D_2O$) and chloroform ($CDCl_3$) for nuclear magnetic resonance (NMR) analysis.

Example 4

Vapor Phase Conversion of 3-Methyloxetan-2-One to Methacrylic Acid Using an H-ZSM-5

Vapor phase conversion of 3-methyloxetan-2-one to methacrylic acid is performed in packed-bed reactor using H-ZSM-5 (Si:Al=38, diameter 2 mm, surface area >=250 $m^2/g$) as a catalyst. 11 grams of H-ZSM-5 catalyst is loaded into jacketed stainless steel 316 pipe reactor (ID 0.5 inch), the catalyst is supported between glass beads columns (stainless steel wool is placed below and above glass beads). Multi-point thermocouple is inserted through the center of the reactor and hot oil is circulated through the reactor jacket to maintain the desired reactor temperature. 3-methyloxetan-2-one is fed to the reactor by means of saturator: $N_2$ at the rate of 28 g/hr is flown into the bottom of the vessel containing liquid 3-methyloxetan-2-one at a=94° C., this results in 3-methyloxetan-2-one feed rate of 5 g/hr. The pressure of reactor and saturator is maintained at 9.5 psig. The reaction products are absorbed in chilled to 10° C. dichloromethane and the solution of reaction products in dichloromethane is analyzed by gas chromatography. The line between the saturator and the reactor as well as the line between the reactor and absorber are heat traced to prevent condensation of 3-methyloxetan-2-one to methacrylic acid. The reaction is conducted at the reactor temperature of 210° C.

Example 5

Conversion of β-Chloromethyl-β-Propiolactone to 4-Chloro-Cis/Trans-2-Butenoic Acid Using a Zeolite This Example describes the production of 4-chloro-cis/trans-2-butenoic acid from the beta-propiolactone reagent exemplified below using a zeolite.

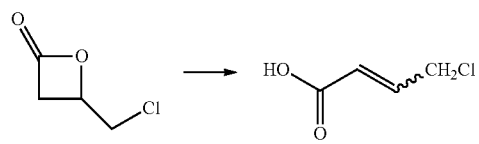

(3)

A mixture of β-chloromethyl-β-propiolactone (3.0 g) and phenothiazine (9.0 mg) is added using a needle valve to a mixture of sulfolane (40.0 g) and Zeolite Y hydrogen (20.0 g) at about 165° C. with 50 psi of carbon monoxide. Zeolite Y hydrogen (80:1 mole ratio $SiO_2/Al_2O_3$, powder S.A. 780 $m^2/g$) is dried under vacuum at about 100° C. for one day before use. Phenothiazine is the polymerization inhibitor used. Sulfolane is the solvent used, and is dried over 3 Å molecular sieves prior to use. β-chloromethyl-β-propiolactone is added slowly using the needle valve over about 8.6 minutes. The reaction mixture is heated to about 170° C. to produce 4-chloro-cis/trans-2-butenoic acid.

The reaction is monitored by infrared spectroscopy (IR). The reaction is completed when no β-chloromethyl-β-propiolactone is detectable by IR.

The zeolite is then filtered off from the reaction mixture, and a sample of the resulting mixture is dissolved in deuterium ($D_2O$) and chloroform ($CDCl_3$) for nuclear magnetic resonance (NMR) analysis.

Example 6

Vapor Phase Conversion of β-Chloromethyl-β-Propiolactone to 4-Chloro-Cis/Trans-2-Butenoic Acid Using an H-ZSM-5

Vapor phase conversion of β-chloromethyl-β-propiolactone to 4-chloro-cis/trans-2-butenoic acid is performed in a packed-bed reactor using H-ZSM-5 (Si:Al=38, diameter 2 mm, surface area >=250 $m^2/g$) as a catalyst. 11 grams of H-ZSM-5 catalyst is loaded into jacketed stainless steel 316 pipe reactor (ID 0.5 inch), the catalyst is supported between glass beads columns (stainless steel wool is placed below and above glass beads). Multi-point thermocouple is inserted through the center of the reactor and hot oil is circulated through the reactor jacket to maintain the desired reactor temperature. β-chloromethyl-β-propiolactone is fed to the reactor by means of saturator: $N_2$ at the rate of about 28 g/hr is flown into the bottom of the vessel containing liquid 4-chloro-trans/cis-2-butenoic acid at a=94° C., this results in 4-chloro-cis/trans-2-butenoic acid feed rate of about 5 g/hr. The pressure of reactor and saturator is maintained at about 9.5 psig. The reaction products are chilled to about 10° C. dichloromethane and the solution of reaction products in dichloromethane is analyzed by gas chromatography. The line between the saturator and the reactor as well as the line between the reactor and absorber are heat traced to prevent condensation of β-chloromethyl-β-propiolactone to 4-chloro-cis/trans-2-butenoic acid. The reaction is conducted at the reactor temperature of about 210° C.

Example 7

Conversion of β-Trifluoromethyl-β-Propiolactone to 4,4,4-Trifluoro-Trans/Cis-2-Butenoic Acid Using a Zeolite This Example describes the production of 4,4,4-trifluoro-cis/trans-2-butenoic acid from the beta-propiolactone reagent exemplified below using a zeolite.

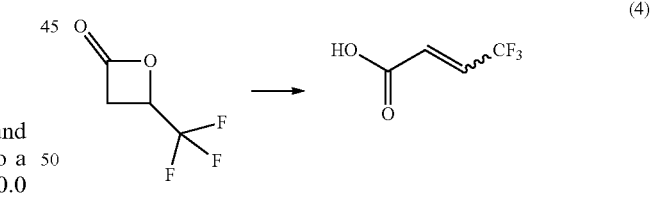

(4)

A mixture of β-trifluoromethyl-β-propiolactone (3.0 g) and phenothiazine (9.0 mg) is added using a needle valve to a mixture of sulfolane (40.0 g) and Zeolite Y hydrogen (20.0 g) at about 165° C. with 50 psi of carbon monoxide. Zeolite Y hydrogen (80:1 mole ratio $SiO_2/Al_2O_3$, powder S.A. 780 $m^2/g$) is dried under vacuum at about 100° C. for one day before use. Phenothiazine is the polymerization inhibitor used. Sulfolane is the solvent used, and is dried over 3 Å molecular sieves prior to use. β-trifluoromethyl-β-propiolactone is added slowly using the needle valve over about 8.6 minutes. The reaction mixture is heated to about 170° C. to produce 4,4,4-trifluoro-cis/trans-2-butenoic acid.

The reaction is monitored by infrared spectroscopy (IR). The reaction is completed when no β-trifluoromethyl-β-propiolactone is detectable by IR.

The zeolite is then filtered off from the reaction mixture, and a sample of the resulting mixture is dissolved in deuterium ($D_2O$) and chloroform ($CDCl_3$) for nuclear magnetic resonance (NMR) analysis.

Example 8

Vapor Phase Conversion of β-Trifluoromethyl-β-Propiolactone to 4,4,4-Trifluoro-Cis/Trans-2-Butenoic Acid Using a H-ZSM-5

Vapor phase conversion of β-trifluoromethyl-β-propiolactone to 4,4,4-trifluoro-cis/trans-2-butenoic acid is performed in packed-bed reactor using H-ZSM-5 (Si:Al=38, diameter 2 mm, surface area >=250 m²/g) as a catalyst. 11 grams of H-ZSM-5 catalyst is loaded into jacketed stainless steel 316 pipe reactor (ID 0.5 inch), the catalyst is supported between glass beads columns (stainless steel wool is placed below and above glass beads). Multi-point thermocouple is inserted through the center of the reactor and hot oil is circulated through the reactor jacket to maintain the desired reactor temperature. β-trifluoromethyl-β-propiolactone is fed to the reactor by means of saturator: $N_2$ at the rate of about 28 g/hr is flown into the bottom of the vessel containing liquid 4,4,4-trifluoro-cis/trans-2-butenoic acid at a=94° C., this results in β-trifluoromethyl-β-propiolactone feed rate of about 5 g/hr. The pressure of reactor and saturator is maintained at about 9.5 psig. The reaction products are absorbed in chilled to about 10° C. dichloromethane and the solution of reaction products in dichloromethane is analyzed by gas chromatography. The line between the saturator and the reactor as well as the line between the reactor and absorber are heat traced to prevent condensation of β-trifluoromethyl-β-propiolactone to 4,4,4-trifluoro-cis/trans-2-butenoic acid. The reaction is conducted at the reactor temperature of about 210° C.

Example 9

Conversion of Various β-Propiolactone Reagents to Organic Acids Using a Zeolite

This Example describes exemplary methods to produce an organic acid from various β-propiolactone reagents using a zeolite. Exemplary reaction schemes are shown below Example 10.

A mixture of a β-propiolactone reagent (3.0 g) and phenothiazine (9.0 mg) is added using a needle valve to a mixture of sulfolane (40.0 g) and Zeolite Y hydrogen (20.0 g) at about 165° C. with 50 psi of carbon monoxide. Zeolite Y hydrogen (80:1 mole ratio $SiO_2/Al_2O_3$, powder S.A. 780 m²/g) is dried under vacuum at about 100° C. for one day before use. Phenothiazine is the polymerization inhibitor used. Sulfolane is the solvent used, and is dried over 3 Å molecular sieves prior to use. The β-propiolactone reagent is added slowly using the needle valve over about 8.6 minutes. The reaction mixture is heated to about 170° C. to produce an organic acid.

The reaction is monitored by infrared spectroscopy (IR). The reaction is completed when no β-propiolactone reagent is detectable by IR.

The zeolite is then filtered off from the reaction mixture, and a sample of the resulting mixture is dissolved in deuterium ($D_2O$) and chloroform ($CDCl_3$) for nuclear magnetic resonance (NMR) analysis.

Example 10

Vapor Phase Conversion of Various β-Propiolactone Reagents to an Organic Acid Using an H-ZSM-5

This Example describes exemplary methods using vapor phase conversion of a β-propiolactone reagent to an organic acid using H-ZSM-5. Exemplary reaction schemes are shown below.

Vapor phase conversion of a substituted β-propiolactone reagents to an organic acid is performed in packed-bed reactor using H-ZSM-5 (Si:Al=38, diameter 2 mm, surface area >=250 m²/g) as a catalyst. 11 grams of H-ZSM-5 catalyst is loaded into jacketed stainless steel 316 pipe reactor (ID 0.5 inch), the catalyst is supported between glass beads columns (stainless steel wool is placed below and above glass beads). Multi-point thermocouple is inserted through the center of the reactor and hot oil is circulated through the reactor jacket to maintain the desired reactor temperature. The β-propiolactone reagent is fed to the reactor by means of saturator: N2 at the rate of about 28 g/hr is flown into the bottom of the vessel containing liquid and organic acid at a=94° C., this results in β-propiolactone reagent feed rate of about 5 g/hr. The pressure of reactor and saturator is maintained at about 9.5 psig. The reaction products are absorbed in chilled to about 10° C. dichloromethane and the solution of reaction products in dichloromethane is analyzed by gas chromatography. The line between the saturator and the reactor as well as the line between the reactor and absorber are heat traced to prevent condensation of the β-propiolactone reagent to an organic acid. The reaction is conducted at the reactor temperature of about 210° C.

Exemplary reaction schemes for converting various beta-propiolactone reagents to their corresponding organic acids are depicted below.

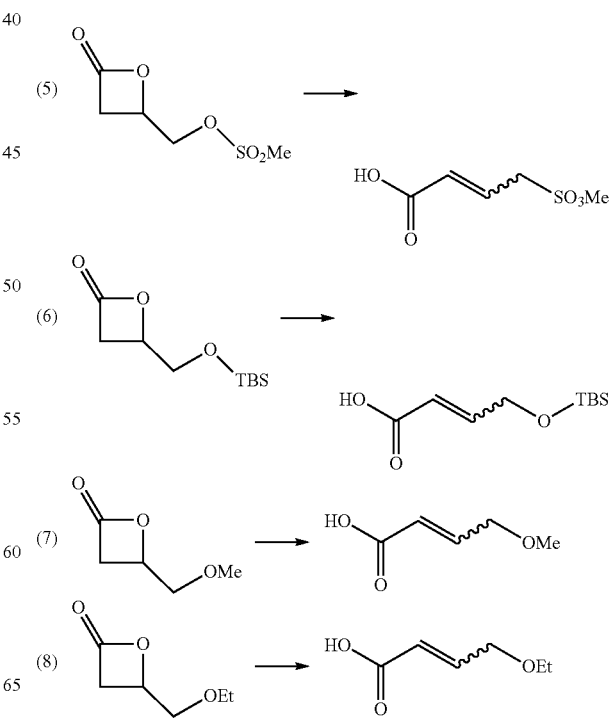

33
-continued
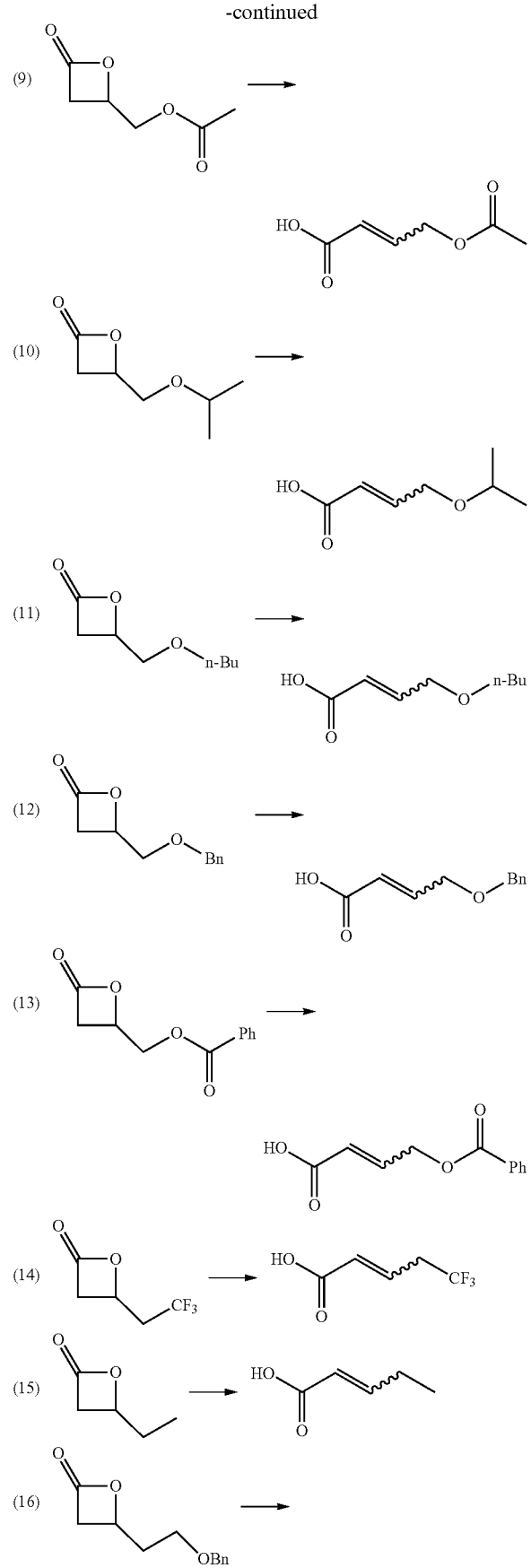
34
-continued
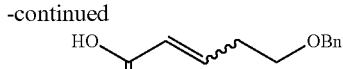
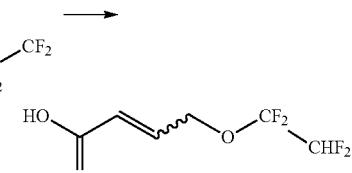
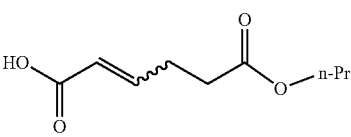
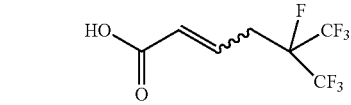
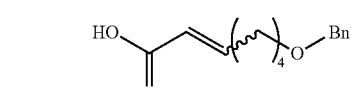
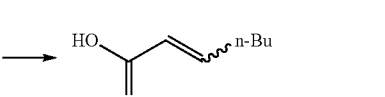
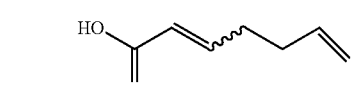
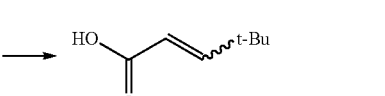

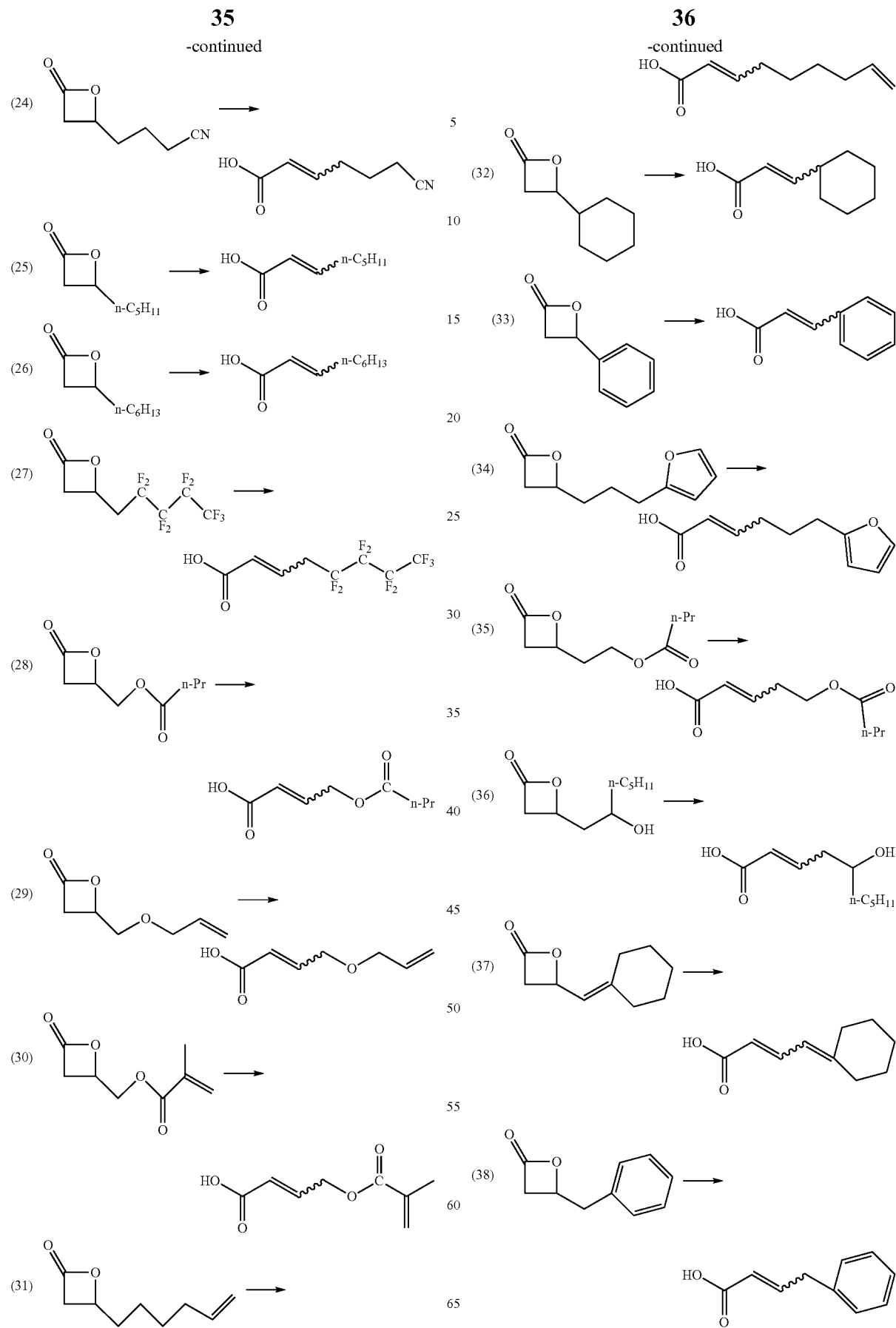

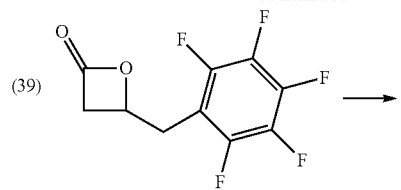
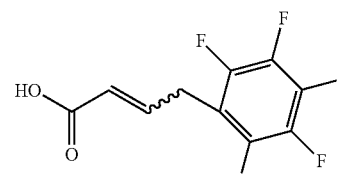
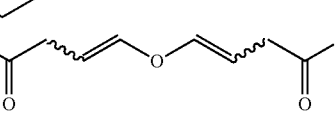
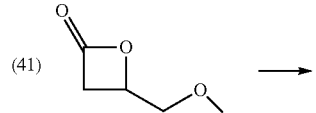
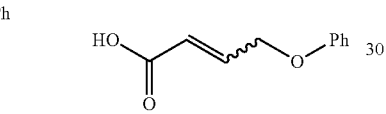
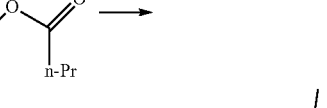
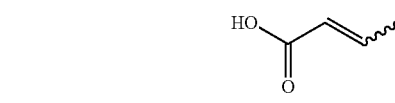
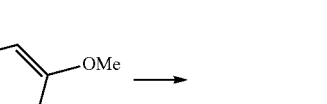
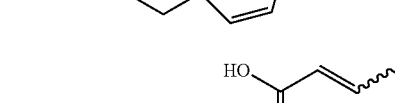
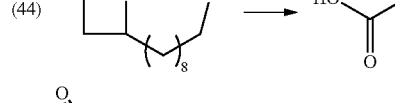
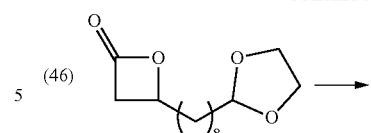
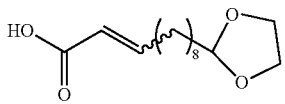
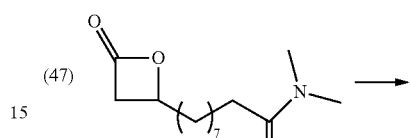
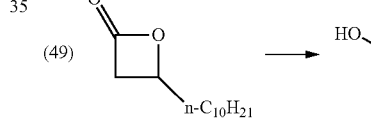
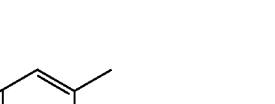
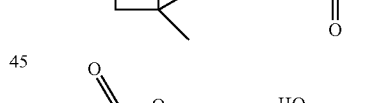
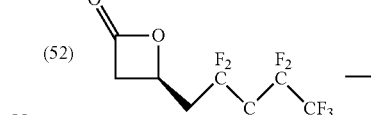
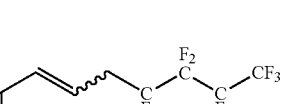
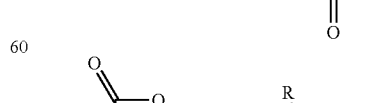

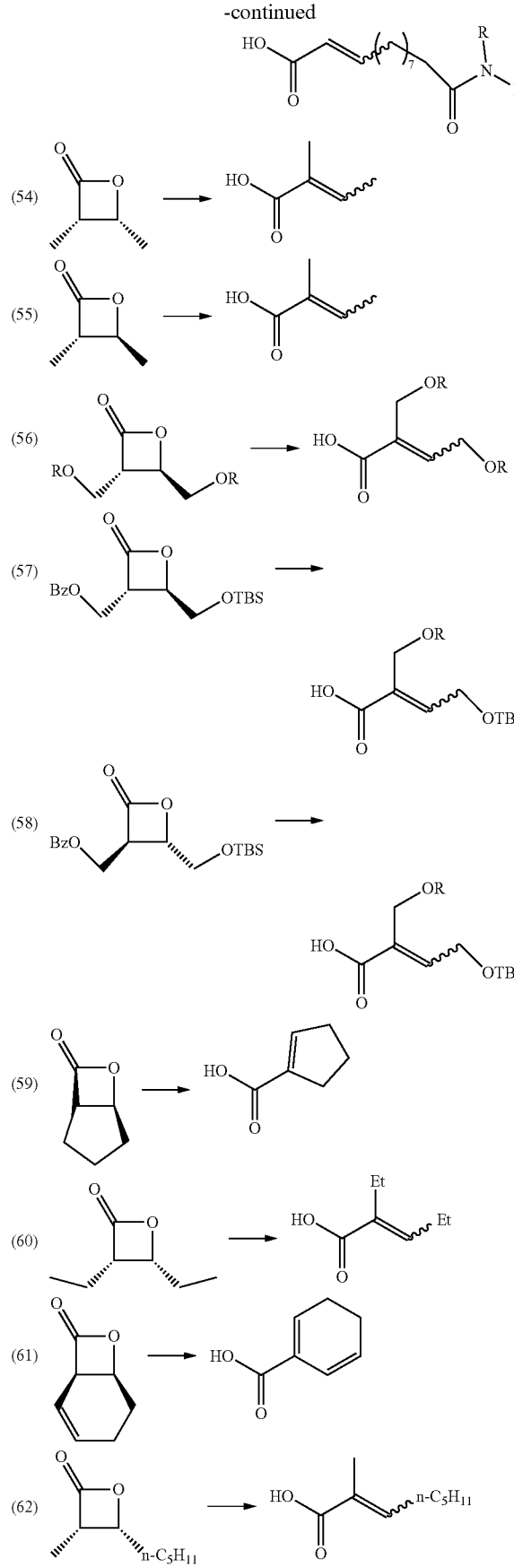
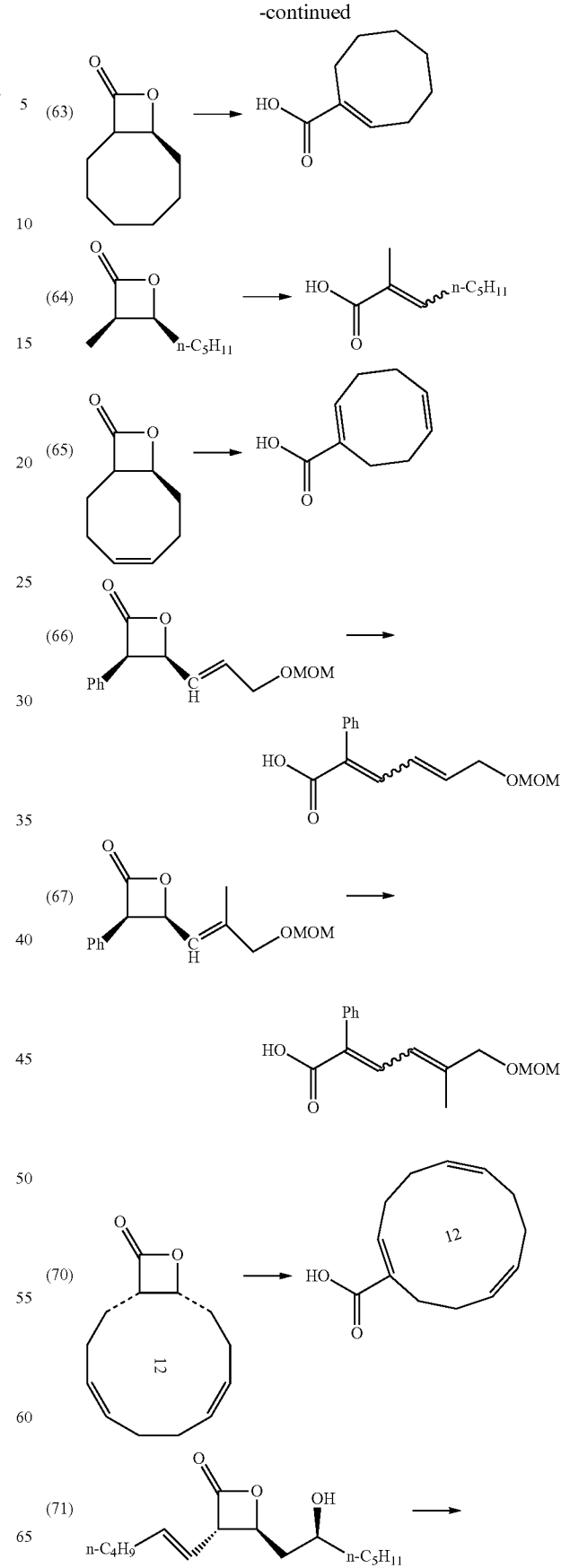

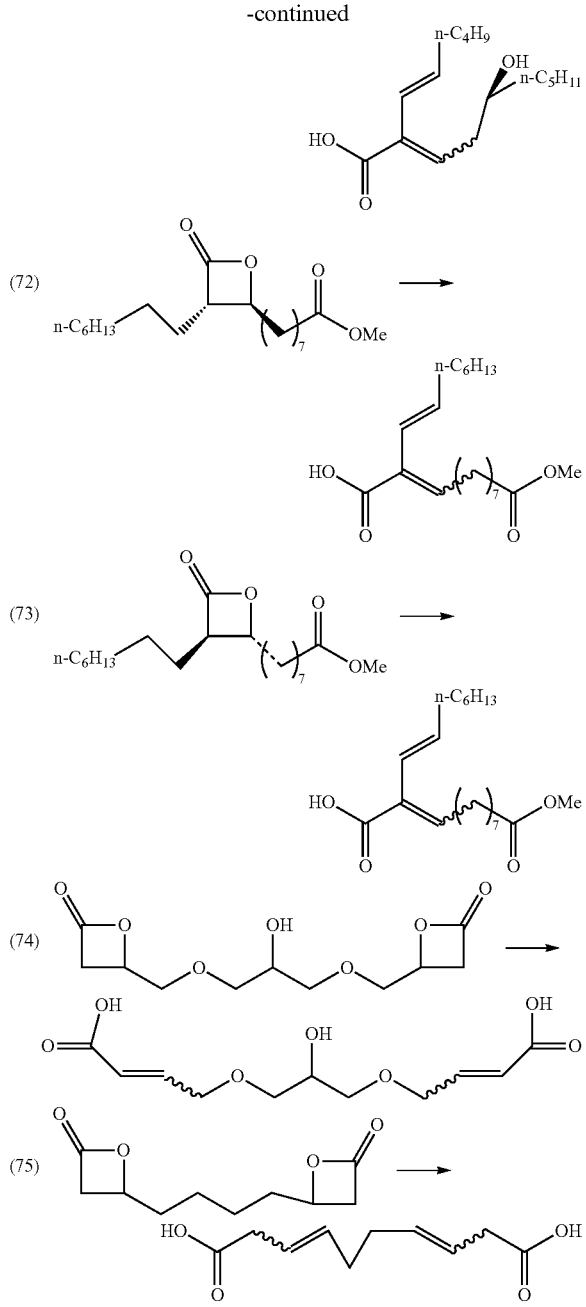

What is claimed:

1. A process for producing an organic acid directly from a beta-lactone reagent, wherein the beta-lactone reagent is represented by the following formula:

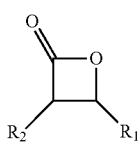

wherein $R_1$ and $R_2$ are independently selected from the group consisting of H, alkyl, alkenyl, alkoxy, alkynyl, cycloalkyl, cycloalkenyl and cycloalkynyl, and wherein both of $R_1$ and $R_2$ are not H at the same time, the method comprising:

introducing the beta-lactone reagent to a reaction vessel;
contacting the beta-lactone reagent with a heterogenous catalyst in the reaction vessel to produce the organic acid; and
removing the organic acid from the reaction vessel, wherein the organic acid is an unsaturated aliphatic carboxylic acid that corresponds to the beta-lactone reagent.

2. The process of claim 1, wherein the heterogenous catalyst comprises a zeolite.

3. The process of claim 2, wherein the zeolite catalyst is in a hydrogen form or in metal cation exchanged form.

4. The process of claim 3, wherein the metal cation is $Na^+$, $K^+$, $Ca^{2+}$, $Mg^{2+}$, $Cu^{2+}$, or $Cu^+$.

5. The process of claim 1, wherein the organic acid is produced continuously.

6. The process of claim 1, wherein the beta-lactone reagent is introduced to the reaction vessel combined with a solvent.

7. The process of claim 1, wherein the reaction vessel further comprises a continuous fixed-bed reactor operating at a pressure between 250 Torr (4.834 psig) and 50 psig.

8. The process of claim 1, wherein the reaction vessel further comprises a continuous fixed-bed reactor configured for receiving the beta-lactone reagent diluted with inert gas.

9. The process of claim 1, wherein the least one reaction vessel further comprises a fluidized bed reactor configured to receive the beta-lactone reagent diluted with nitrogen.

10. The process of claim 1, wherein the least one reaction vessel further comprises a tubular shell-and-tube reactor with a heterogenous catalyst loaded into the tubes and heat transfer fluid fed to the shell side to facilitate temperature control and removal of the heat produced during the reactions.

11. The process of claim 1, wherein the organic acid is continuously isolated.

12. The process of claim 1, wherein the organic acid is produced at a yield of at least 50%.

13. The process of claim 1, wherein the organic acid is produced at a temperature between 100° C. and 300° C.

14. The process of claim 1, wherein one of $R_1$ and $R_2$ is H, and the other of $R_1$ and $R_2$ is alkyl.

15. The process of claim 14, wherein $R_1$ is alkyl, and $R_2$ is H.

16. A process for producing an organic acid directly from a beta-lactone reagent, wherein the beta-lactone reagent is a substituted beta-propiolactone represented by the following formula:

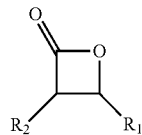

wherein $R_1$ and $R_2$ are independently selected from the group consisting of H, alkyl, alkenyl, alkoxy, alkynyl, cycloalkyl, cycloalkenyl and cycloalkynyl, and wherein both of $R_1$ and $R_2$ are not H at the same time, the method comprising:

introducing the beta-lactone reagent to a reaction vessel;
contacting the beta-lactone reagent with a heterogenous catalyst, wherein the heterogenous catalyst is a zeolite, in the reaction vessel to produce the organic acid; and
removing organic acid from the reaction vessel, wherein the organic acid is an unsaturated aliphatic carboxylic acid that corresponds to the substituted beta-propiolactone.

17. The process of claim 16, wherein the zeolite catalyst is in a hydrogen form or in metal cation exchanged form.

18. The process of claim 16, wherein the beta-lactone reagent is introduced to the reaction vessel combined with a solvent.

19. The process of claim 16, wherein the reaction vessel further comprises a continuous fixed-bed reactor configured for receiving the beta-lactone reagent diluted with inert gas.

20. A process for producing an organic acid directly from a beta-lactone reagent, wherein the beta-lactone reagent is a substituted beta-propiolactone represented by the following formula:

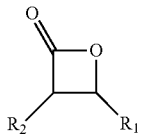

wherein $R_1$ and $R_2$ are independently selected from the group consisting of H, alkyl, alkenyl, alkoxy, alkynyl, cycloalkyl, cycloalkenyl and cycloalkynyl, and wherein both of $R_1$ and $R_2$ are not H at the same time and one of $R_1$ and $R_2$ is H, the method comprising:

introducing the beta-lactone reagent to a reaction vessel;

contacting the beta-lactone reagent with a heterogenous catalyst, wherein the heterogenous catalyst is a zeolite, in the reaction vessel to produce the organic acid; and removing organic acid from the reaction vessel, wherein the organic acid is an unsaturated aliphatic carboxylic acid that corresponds to the substituted beta-propiolactone.

* * * * *

UNITED STATES PATENT AND TRADEMARK OFFICE
CERTIFICATE OF CORRECTION

PATENT NO. : 12,152,004 B2
APPLICATION NO. : 17/054811
DATED : November 26, 2024
INVENTOR(S) : Sadesh H. Sookraj It is certified that error appears in the above-identified patent and that said Letters Patent is hereby corrected as shown below:

In the Specification

Column 1, Line 10, "29 Jun. 2019" should be —25 Jun. 2019—

In the Claims

Column 42, Claim 9, Line 27, "the least one" should be —the—

Column 42, Claim 10, Line 30, "the least one" should be —the—

Column 42, Claim 16, Line 59, "organic acid" should be —the organic acid—

Column 44, Claim 20, Line 11, "organic acid" should be —the organic acid—

Signed and Sealed this
Fourth Day of November, 2025

John A. Squires
*Director of the United States Patent and Trademark Office*